US011324424B2

(12) United States Patent
Grubb et al.

(10) Patent No.: US 11,324,424 B2
(45) Date of Patent: May 10, 2022

(54) APPARATUS AND METHOD FOR IMAGING BLOOD IN A TARGET REGION OF TISSUE

(71) Applicant: Smith & Nephew PLC, Watford (GB)

(72) Inventors: Scott Grubb, Cambridge (GB); Allan Kenneth Frazer Grugeon Hunt, Beverley (GB); Peter Laitenberger, Cambridge (GB)

(73) Assignee: Smith & Nephew PLC, Watford (GB)

( * ) Notice: Subject to any disclaimer, the term of this patent is extended or adjusted under 35 U.S.C. 154(b) by 214 days.

(21) Appl. No.: 16/491,959

(22) PCT Filed: Mar. 9, 2018

(86) PCT No.: PCT/EP2018/055945
§ 371 (c)(1),
(2) Date: Sep. 6, 2019

(87) PCT Pub. No.: WO2018/162732
PCT Pub. Date: Sep. 13, 2018

(65) Prior Publication Data
US 2020/0281513 A1    Sep. 10, 2020

(30) Foreign Application Priority Data

Mar. 9, 2017 (GB) ..................... 1703771
Mar. 9, 2017 (GB) ..................... 1703772

(51) Int. Cl.
*A61B 5/1455*   (2006.01)
*A61B 5/00*     (2006.01)

(52) U.S. Cl.
CPC .......... *A61B 5/14558* (2013.01); *A61B 5/489* (2013.01); *A61B 5/6898* (2013.01); *A61B 2560/0431* (2013.01); *A61B 2562/046* (2013.01)

(58) Field of Classification Search
CPC ... A61B 5/489; A61B 5/1455; A61B 5/14551; A61B 5/14552; A61B 5/14532;
(Continued)

(56) References Cited

U.S. PATENT DOCUMENTS 3,896,802 A   7/1975 Wiliams
4,334,530 A   6/1982 Hassell
(Continued)

FOREIGN PATENT DOCUMENTS

CN   105232229   1/2016
CN   105395184   3/2016
(Continued)

OTHER PUBLICATIONS

"Little Miss Plasters", kidstravelclub.co.uk., accessed Aug. 26, 2016, in 2 pages. URL: http://www.kidstravelclub.co.uk/little-miss-girls-childrens-plasters.

(Continued)

*Primary Examiner* — Chu Chuan Liu
(74) *Attorney, Agent, or Firm* — Knobbe, Martens, Olson & Bear, LLP

(57) ABSTRACT

In some embodiments, an apparatus for imaging blood within a target region of tissue includes an imaging device configured to output image data associated with light received by the imaging device having a first and second spectral ranges, wherein the absorptivity by blood of light having the first spectral range is less than the absorptivity by blood of light having the second spectral range, and a controlling element configured to capture the image data associated with light received by the imaging device and to process the captured image data associated with light having the first spectral range and the captured image data associated with light having the second spectral range to generate (Continued)

compound image data associated with an amount of blood within the target region of tissue.

22 Claims, 12 Drawing Sheets

(58) Field of Classification Search
CPC .............. A61B 5/14546; A61B 5/6898; A61B 5/14558; A61B 2562/046; A61B 2561/0431
See application file for complete search history.

(56) References Cited

U.S. PATENT DOCUMENTS

| | | | |
|---|---|---|---|
| 5,090,410 A | 2/1992 | Saper et al. |
| 5,253,654 A | 10/1993 | Thomas et al. |
| 5,635,201 A | 6/1997 | Fabo |
| 5,642,096 A | 6/1997 | Leyerer et al. |
| 5,678,448 A | 10/1997 | Fallen et al. |
| 5,690,610 A | 11/1997 | Ito et al. |
| 5,836,990 A | 11/1998 | Li |
| 6,095,992 A | 8/2000 | Augustine |
| 6,178,342 B1 | 1/2001 | Borgos et al. |
| 6,381,482 B1 | 4/2002 | Jayaraman et al. |
| 6,517,484 B1 | 2/2003 | Wilk et al. |
| 6,551,252 B2 | 4/2003 | Sackner et al. |
| 6,731,987 B1 | 5/2004 | McAdams et al. |
| 7,077,832 B2 | 7/2006 | Fleischmann |
| 7,088,591 B2 | 8/2006 | Kishimoto et al. |
| 7,201,063 B2 | 4/2007 | Taylor et al. |
| 7,206,623 B2 | 4/2007 | Blank et al. |
| 7,289,205 B2 | 10/2007 | Yaroslavsky et al. |
| 7,316,652 B2 | 1/2008 | Dalgaard et al. |
| 7,429,255 B2 | 9/2008 | Thompson |
| 7,520,875 B2 | 4/2009 | Bernabei |
| 7,521,292 B2 | 4/2009 | Rogers et al. |
| 7,569,742 B2 | 8/2009 | Haggstrom et al. |
| 7,625,117 B2 | 12/2009 | Haslett et al. |
| 7,687,678 B2 | 3/2010 | Jacobs |
| 7,838,717 B2 | 11/2010 | Haggstrom et al. |
| 7,846,141 B2 | 12/2010 | Weston |
| 7,877,866 B1 | 2/2011 | Greenberg et al. |
| 7,884,258 B2 | 2/2011 | Boehringer et al. |
| 7,904,133 B2 | 3/2011 | Gehman et al. |
| 7,922,676 B2 | 4/2011 | Daskal et al. |
| 7,942,869 B2 | 5/2011 | Houbolt et al. |
| 7,945,302 B2 | 5/2011 | McAdams |
| 8,019,401 B1 | 9/2011 | Smith et al. |
| 8,032,210 B2 | 10/2011 | Finneran et al. |
| 8,060,174 B2 | 11/2011 | Simpson et al. |
| 8,079,247 B2 | 12/2011 | Russell et al. |
| 8,111,165 B2 | 2/2012 | Ortega et al. |
| 8,116,841 B2 | 2/2012 | Bly et al. |
| 8,182,425 B2 | 5/2012 | Stamatas et al. |
| 8,207,392 B2 | 6/2012 | Haggstrom et al. |
| 8,238,996 B2 | 8/2012 | Burnes |
| 8,241,231 B2 | 8/2012 | Bausewein et al. |
| 8,332,053 B1 | 12/2012 | Patterson et al. |
| 8,333,874 B2 | 12/2012 | Currie et al. |
| 8,366,692 B2 | 2/2013 | Weston |
| 8,480,641 B2 | 7/2013 | Jacobs |
| 8,579,872 B2 | 11/2013 | Coulthard et al. |
| 8,644,911 B1 | 2/2014 | Panasyuk et al. |
| 8,663,106 B2 | 3/2014 | Stivoric et al. |
| 8,682,442 B2 | 3/2014 | McAdams |
| 8,783,948 B2 | 7/2014 | Panda et al. |
| 8,788,009 B2 | 7/2014 | Greene et al. |
| 8,800,386 B2 | 8/2014 | Taylor |
| 8,818,478 B2 | 8/2014 | Scheffler et al. |
| 8,829,263 B2 | 9/2014 | Haggstrom et al. |
| 8,848,187 B2 | 9/2014 | Uematsu et al. |
| 8,894,590 B2 | 11/2014 | Lamoise et al. |
| 8,925,392 B2 | 1/2015 | Esposito et al. |
| 8,934,957 B2 | 1/2015 | Dias et al. |
| 8,934,965 B2 | 1/2015 | Rogers et al. |
| 8,943,897 B2 | 2/2015 | Beauvais et al. |
| 8,948,839 B1 | 2/2015 | Longinotti-Buitoni et al. |
| 8,974,428 B2 | 3/2015 | Shuler et al. |
| 8,997,588 B2 | 4/2015 | Taylor |
| 9,000,251 B2 | 4/2015 | Murphy et al. |
| 9,042,075 B2 | 5/2015 | Borini et al. |
| 9,192,531 B2 | 11/2015 | Wu |
| 9,192,700 B2 | 11/2015 | Weston et al. |
| 9,204,806 B2 | 12/2015 | Stivoric et al. |
| 9,220,455 B2 | 12/2015 | Sarrafzadeh et al. |
| 9,226,402 B2 | 12/2015 | Hsu |
| 9,282,897 B2 | 3/2016 | Ross, Jr. et al. |
| 9,314,175 B2 | 4/2016 | Jacofsky et al. |
| 9,320,473 B2 | 4/2016 | Shuler |
| 9,372,123 B2 | 6/2016 | Li et al. |
| 9,378,450 B1 | 6/2016 | Mei et al. |
| 9,386,947 B2 | 7/2016 | Johnson |
| 9,393,354 B2 | 7/2016 | Freedman et al. |
| 9,402,988 B2 | 8/2016 | Buchanan et al. |
| 9,408,573 B2 | 8/2016 | Welch et al. |
| 9,427,179 B2 | 8/2016 | Mestrovic et al. |
| 9,439,599 B2 | 9/2016 | Thompson et al. |
| 9,483,726 B2 | 11/2016 | Mei et al. |
| 9,494,474 B2 | 11/2016 | Servati et al. |
| 9,511,215 B2 | 12/2016 | Skiba |
| 9,516,758 B2 | 12/2016 | Arora et al. |
| 9,526,439 B2 | 12/2016 | Connelly et al. |
| 9,554,484 B2 | 1/2017 | Rogers et al. |
| 9,572,507 B2 | 2/2017 | Moore et al. |
| 9,582,072 B2 | 2/2017 | Connor |
| 9,585,620 B2 | 3/2017 | Paquet et al. |
| 9,587,991 B2 | 3/2017 | Padiy |
| 9,592,007 B2 | 3/2017 | Nuovo et al. |
| 9,603,560 B2 | 3/2017 | Monty et al. |
| 9,610,388 B2 | 4/2017 | Aceto et al. |
| 9,613,911 B2 | 4/2017 | Rogers et al. |
| 9,629,584 B2 | 4/2017 | Barber et al. |
| 9,675,238 B2 | 6/2017 | Iida et al. |
| 9,687,195 B2 | 6/2017 | Sims et al. |
| 9,717,565 B2 | 8/2017 | Blair |
| 9,829,471 B2 | 11/2017 | Hammond et al. |
| 9,907,103 B2 | 2/2018 | Chen et al. |
| 9,999,711 B2 | 6/2018 | Weston et al. |
| 10,004,643 B2 | 6/2018 | Luckemeyer et al. |
| 10,046,096 B2 | 8/2018 | Askem et al. |
| 10,080,524 B1 | 9/2018 | Xi |
| 10,086,117 B2 | 10/2018 | Locke et al. |
| 10,117,705 B2 | 11/2018 | Chernov et al. |
| 10,152,789 B2 | 12/2018 | Carnes et al. |
| 10,182,740 B2 | 1/2019 | Tonar et al. |
| 10,201,644 B2 | 2/2019 | Haggstrom et al. |
| 10,207,031 B2 | 2/2019 | Toth |
| 10,209,213 B2 | 2/2019 | Kang et al. |
| 10,285,620 B2 | 5/2019 | Jung et al. |
| 10,288,590 B2 | 5/2019 | Hammond et al. |
| 10,321,862 B2 | 6/2019 | Dalene et al. |
| 10,463,773 B2 | 11/2019 | Haggstrom et al. |
| 10,857,038 B2 | 12/2020 | Zamierowski et al. |
| 11,026,847 B2 | 6/2021 | Piotrowski et al. |
| 2002/0016536 A1 | 2/2002 | Benni |
| 2002/0135752 A1 | 9/2002 | Sokolov et al. |
| 2003/0033032 A1 | 2/2003 | Lind et al. |
| 2003/0036751 A1* | 2/2003 | Anderson ............. A61B 5/489 128/898 |
| 2003/0208148 A1 | 11/2003 | Sullivan |
| 2003/0210810 A1 | 11/2003 | Gee, Jr. et al. |
| 2003/0216630 A1 | 11/2003 | Jersey-Willuhn et al. |
| 2004/0034293 A1 | 2/2004 | Kimball |
| 2004/0230132 A1 | 11/2004 | Shehada |
| 2005/0088832 A1 | 4/2005 | Su et al. |
| 2005/0240107 A1 | 10/2005 | Alfano et al. |
| 2005/0280531 A1 | 12/2005 | Fadem et al. |
| 2005/0281445 A1* | 12/2005 | Marcotte ................ A61B 5/489 382/128 |
| 2006/0052678 A1 | 3/2006 | Drinan et al. |
| 2006/0058690 A1 | 3/2006 | Bartnik et al. |
| 2006/0181791 A1 | 8/2006 | Van Beek et al. |
| 2006/0234383 A1 | 10/2006 | Gough |
| 2006/0241495 A1 | 10/2006 | Kurtz |

(56) References Cited

U.S. PATENT DOCUMENTS

| | | |
|---|---|---|
| 2007/0055209 A1 | 3/2007 | Patel et al. |
| 2007/0173892 A1 | 7/2007 | Fleischer et al. |
| 2007/0191754 A1 | 8/2007 | Aali |
| 2007/0260421 A1 | 11/2007 | Berner, Jr. et al. |
| 2007/0293748 A1 | 12/2007 | Engvall et al. |
| 2008/0081973 A1 | 4/2008 | Hoarau |
| 2008/0167535 A1 | 7/2008 | Stivoric et al. |
| 2008/0258717 A1 | 10/2008 | Igney et al. |
| 2008/0287747 A1 | 11/2008 | Mestrovic et al. |
| 2008/0319282 A1 | 12/2008 | Tran |
| 2008/0319283 A1 | 12/2008 | Cotton et al. |
| 2009/0149800 A1 | 6/2009 | Durand |
| 2009/0177051 A1 | 7/2009 | Arons et al. |
| 2009/0177110 A1 | 7/2009 | Lyden et al. |
| 2009/0209830 A1 | 8/2009 | Nagle et al. |
| 2009/0234206 A1 | 9/2009 | Gaspard et al. |
| 2009/0245601 A1 | 10/2009 | Cohen et al. |
| 2010/0022990 A1 | 1/2010 | Karpowicz et al. |
| 2010/0025831 A1 | 2/2010 | Yamazaki et al. |
| 2010/0166252 A1 | 7/2010 | Ahmed et al. |
| 2010/0168727 A1 | 7/2010 | Hancock et al. |
| 2010/0268111 A1 | 10/2010 | Drinan et al. |
| 2010/0305473 A1 | 12/2010 | Yuzhakov |
| 2011/0004088 A1 | 1/2011 | Grossman |
| 2011/0015591 A1 | 1/2011 | Hanson et al. |
| 2011/0054283 A1 | 3/2011 | Shuler |
| 2011/0092958 A1 | 4/2011 | Jacobs |
| 2011/0130697 A1 | 6/2011 | Nagle et al. |
| 2011/0140703 A1 | 6/2011 | Chiao et al. |
| 2011/0190639 A1 | 8/2011 | Peltie et al. |
| 2011/0218757 A1 | 9/2011 | Callsen et al. |
| 2011/0242532 A1 | 10/2011 | McKenna |
| 2011/0245682 A1 | 10/2011 | Robinson et al. |
| 2011/0301441 A1 | 12/2011 | Bandic et al. |
| 2012/0029306 A1 | 2/2012 | Paquet et al. |
| 2012/0029307 A1 | 2/2012 | Paquet et al. |
| 2012/0029410 A1 | 2/2012 | Koenig et al. |
| 2012/0112347 A1 | 5/2012 | Eckhardt et al. |
| 2012/0165717 A1 | 6/2012 | Al Khaburi et al. |
| 2012/0166680 A1* | 6/2012 | Masoud ............. A61B 5/0022 710/8 |
| 2012/0190956 A1 | 7/2012 | Connolly |
| 2012/0190989 A1 | 7/2012 | Kaiser et al. |
| 2012/0265120 A1 | 10/2012 | Beisang, III et al. |
| 2012/0271265 A1 | 10/2012 | Langdon |
| 2012/0277559 A1 | 11/2012 | Kohl-Bareis et al. |
| 2012/0316538 A1 | 12/2012 | Heiser et al. |
| 2012/0330252 A1 | 12/2012 | Stokes et al. |
| 2013/0041235 A1 | 2/2013 | Rogers et al. |
| 2013/0064772 A1 | 3/2013 | Swiss et al. |
| 2013/0121544 A1 | 5/2013 | Sarrafzadeh et al. |
| 2013/0123722 A1 | 5/2013 | Pratt et al. |
| 2013/0151223 A1 | 6/2013 | Zamierowski et al. |
| 2013/0200268 A1 | 8/2013 | Rafferty et al. |
| 2013/0261409 A1 | 10/2013 | Pathak et al. |
| 2013/0271278 A1 | 10/2013 | Duesterhof et al. |
| 2013/0274629 A1 | 10/2013 | Duesterhoft et al. |
| 2013/0317367 A1 | 11/2013 | Shuler |
| 2014/0012108 A1 | 1/2014 | McPeak |
| 2014/0018637 A1 | 1/2014 | Bennett et al. |
| 2014/0024905 A1 | 1/2014 | Sarrafzadeh et al. |
| 2014/0031663 A1 | 1/2014 | Gallego et al. |
| 2014/0072190 A1 | 3/2014 | Wu et al. |
| 2014/0075658 A1 | 3/2014 | McGuin |
| 2014/0107495 A1 | 4/2014 | Marinelli et al. |
| 2014/0107498 A1 | 4/2014 | Bower et al. |
| 2014/0147611 A1 | 5/2014 | Ackerman, Jr. et al. |
| 2014/0203797 A1 | 7/2014 | Stivoric et al. |
| 2014/0206947 A1 | 7/2014 | Isserow et al. |
| 2014/0232516 A1 | 8/2014 | Stivoric et al. |
| 2014/0235166 A1 | 8/2014 | Molettiere et al. |
| 2014/0243709 A1 | 8/2014 | Gibson et al. |
| 2014/0296749 A1 | 10/2014 | Reid, Jr. et al. |
| 2014/0298927 A1 | 10/2014 | Allin et al. |
| 2014/0298928 A1 | 10/2014 | Duesterhoft et al. |
| 2014/0303463 A1 | 10/2014 | Robinson et al. |
| 2014/0324120 A1 | 10/2014 | Bogie et al. |
| 2014/0340857 A1 | 11/2014 | Hsu et al. |
| 2014/0343478 A1 | 11/2014 | Brennan et al. |
| 2014/0350882 A1 | 11/2014 | Everett et al. |
| 2015/0018792 A1 | 1/2015 | Marsiquet et al. |
| 2015/0025343 A1 | 1/2015 | Gareau et al. |
| 2015/0138330 A1 | 5/2015 | Krishnamoorthi |
| 2015/0141767 A1 | 5/2015 | Rogers et al. |
| 2015/0148760 A1 | 5/2015 | Dodd et al. |
| 2015/0150479 A1 | 6/2015 | Yoshino et al. |
| 2015/0182166 A1 | 7/2015 | Evans et al. |
| 2015/0223716 A1 | 8/2015 | Korkala et al. |
| 2015/0257644 A1 | 9/2015 | Cao |
| 2015/0265191 A1 | 9/2015 | Harding et al. |
| 2015/0292968 A1 | 10/2015 | Vogt et al. |
| 2015/0313476 A1 | 11/2015 | Pisani et al. |
| 2015/0313533 A1 | 11/2015 | Rapp et al. |
| 2015/0327777 A1 | 11/2015 | Kostic et al. |
| 2015/0335254 A1 | 11/2015 | Fastert et al. |
| 2015/0335287 A1 | 11/2015 | Neuman et al. |
| 2015/0335288 A1 | 11/2015 | Toth et al. |
| 2015/0351970 A1 | 12/2015 | Dagger et al. |
| 2015/0359485 A1 | 12/2015 | Berg et al. |
| 2015/0374309 A1 | 12/2015 | Farkas et al. |
| 2016/0015962 A1 | 1/2016 | Shokoueinejad Maragheh |
| 2016/0022223 A1 | 1/2016 | Grundfest et al. |
| 2016/0029900 A1 | 2/2016 | LaPlante et al. |
| 2016/0030132 A1 | 2/2016 | Cheung et al. |
| 2016/0038045 A1 | 2/2016 | Shapiro |
| 2016/0038083 A1 | 2/2016 | Ding et al. |
| 2016/0051147 A1 | 2/2016 | Cohen et al. |
| 2016/0058380 A1 | 3/2016 | Lee et al. |
| 2016/0066854 A1 | 3/2016 | Mei et al. |
| 2016/0069743 A1 | 3/2016 | McQuilkin et al. |
| 2016/0074234 A1 | 3/2016 | Abichandi et al. |
| 2016/0081580 A1 | 3/2016 | Bergelin et al. |
| 2016/0081601 A1 | 3/2016 | Ballam et al. |
| 2016/0100790 A1 | 4/2016 | Cantu et al. |
| 2016/0100987 A1 | 4/2016 | Hartwell et al. |
| 2016/0101282 A1 | 4/2016 | Bergelin et al. |
| 2016/0129469 A1 | 5/2016 | Kulinsky et al. |
| 2016/0143534 A1 | 5/2016 | Hyde et al. |
| 2016/0157779 A1 | 6/2016 | Baxi et al. |
| 2016/0165719 A1 | 6/2016 | Li et al. |
| 2016/0166438 A1 | 6/2016 | Rovaniemi |
| 2016/0213269 A1 | 7/2016 | Lam et al. |
| 2016/0228049 A1 | 8/2016 | Nackaerts et al. |
| 2016/0232807 A1 | 8/2016 | Ghaffari et al. |
| 2016/0242331 A1 | 8/2016 | Park et al. |
| 2016/0249810 A1 | 9/2016 | Darty et al. |
| 2016/0262672 A1 | 9/2016 | Hammond et al. |
| 2016/0262687 A1 | 9/2016 | Vaidyanathan et al. |
| 2016/0270700 A1 | 9/2016 | Baxi et al. |
| 2016/0287177 A1 | 10/2016 | Huppert et al. |
| 2016/0302729 A1 | 10/2016 | Starr et al. |
| 2016/0310023 A1 | 10/2016 | Chachisvilis et al. |
| 2016/0317057 A1 | 11/2016 | Li et al. |
| 2016/0331263 A1 | 11/2016 | Cailler et al. |
| 2016/0331322 A1 | 11/2016 | Son et al. |
| 2016/0338591 A1 | 11/2016 | Lachenbruch et al. |
| 2016/0354001 A1 | 12/2016 | Buckley et al. |
| 2016/0367189 A1 | 12/2016 | Aimone et al. |
| 2016/0367192 A1 | 12/2016 | Iyengar et al. |
| 2016/0367406 A1 | 12/2016 | Barnett |
| 2017/0000407 A1 | 1/2017 | Saxby et al. |
| 2017/0007853 A1 | 1/2017 | Alford et al. |
| 2017/0027498 A1 | 2/2017 | Larson et al. |
| 2017/0079740 A1 | 3/2017 | Hufnagel et al. |
| 2017/0086519 A1 | 3/2017 | Vigano et al. |
| 2017/0086709 A1 | 3/2017 | Khine et al. |
| 2017/0095208 A1 | 4/2017 | Oberleitner et al. |
| 2017/0146474 A1 | 5/2017 | Bedell et al. |
| 2017/0156594 A1 | 6/2017 | Stivoric et al. |
| 2017/0156621 A1 | 6/2017 | Bettinger et al. |
| 2017/0156658 A1 | 6/2017 | Maharbiz et al. |
| 2017/0164865 A1 | 6/2017 | Rafferty et al. |
| 2017/0164876 A1 | 6/2017 | Hyde et al. |
| 2017/0172439 A1 | 6/2017 | Zhu et al. |

(56) References Cited

U.S. PATENT DOCUMENTS

| | | |
|---|---|---|
| 2017/0202711 A1 | 7/2017 | Cernasov et al. |
| 2017/0224271 A1 | 8/2017 | Lachenbruch et al. |
| 2017/0231015 A1 | 8/2017 | Jang et al. |
| 2017/0258972 A1 | 9/2017 | Weston |
| 2017/0304510 A1 | 10/2017 | Askem et al. |
| 2017/0319075 A1 | 11/2017 | Homan et al. |
| 2017/0326004 A1 | 11/2017 | Long et al. |
| 2017/0367644 A1 | 12/2017 | Sharman et al. |
| 2018/0008177 A1 | 1/2018 | Shimuta et al. |
| 2018/0055359 A1 | 3/2018 | Shamim et al. |
| 2018/0055697 A1 | 3/2018 | Mihail et al. |
| 2018/0056087 A1 | 3/2018 | Ribiero et al. |
| 2018/0070880 A1 | 3/2018 | Trembly et al. |
| 2018/0074547 A1 | 3/2018 | Smadi et al. |
| 2018/0116877 A1 | 5/2018 | Ineichen |
| 2018/0128681 A1 | 5/2018 | Otsuka |
| 2018/0132287 A1 | 5/2018 | Cheng et al. |
| 2018/0192514 A1 | 7/2018 | Seo |
| 2018/0200414 A1 | 7/2018 | Askem et al. |
| 2018/0206758 A1 | 7/2018 | Feldkamp et al. |
| 2018/0235484 A1 | 8/2018 | Mozdzierz |
| 2018/0296397 A1 | 10/2018 | Askem et al. |
| 2019/0001032 A1 | 1/2019 | Weston et al. |
| 2019/0021911 A1 | 1/2019 | Askem et al. |
| 2019/0060126 A1 | 2/2019 | Ribble et al. |
| 2019/0076298 A1 | 3/2019 | Quintanar et al. |
| 2019/0083025 A1 | 3/2019 | Aung et al. |
| 2019/0133812 A1 | 5/2019 | Seres et al. |
| 2019/0134280 A1 | 5/2019 | Toth |
| 2019/0159938 A1 | 5/2019 | Askem et al. |
| 2019/0175098 A1 | 6/2019 | Burns |
| 2019/0192066 A1 | 6/2019 | Schoess et al. |
| 2019/0231939 A1 | 8/2019 | Askem et al. |
| 2019/0290496 A1 | 9/2019 | Brownhill et al. |
| 2020/0147407 A1 | 5/2020 | Efremkin |
| 2020/0330258 A1 | 10/2020 | Hansen et al. |

FOREIGN PATENT DOCUMENTS

| | | |
|---|---|---|
| CN | 106102322 | 11/2016 |
| DE | 10 2012 211015 | 1/2014 |
| DE | 102013 013013 | 2/2015 |
| EP | 2 005 886 | 12/2008 |
| EP | 2 454 990 | 5/2012 |
| EP | 2 565 630 | 3/2013 |
| EP | 2 574 275 | 4/2013 |
| EP | 1 734 858 | 7/2014 |
| EP | 3034054 A1 | 6/2016 |
| EP | 3 231 478 | 10/2017 |
| EP | 3 409 190 | 12/2018 |
| EP | 3 499 510 | 6/2019 |
| GB | 1476894 | 6/1977 |
| GB | 2316171 | 2/1998 |
| GB | 2563602 | 12/2018 |
| JP | 2009-225863 | 10/2009 |
| KR | 10 2012 0119523 | 10/2012 |
| KR | 101224629 B1 | 1/2013 |
| KR | 10 2014 0024743 | 3/2014 |
| KR | 10 2014 0058041 | 5/2014 |
| KR | 10 2016 0071044 | 6/2016 |
| KR | 20190105898 A | 9/2019 |
| NL | 1 027 236 | 4/2006 |
| WO | WO 2000/021433 | 4/2000 |
| WO | WO 2000/043046 | 7/2000 |
| WO | WO 2003/067229 | 8/2003 |
| WO | WO 2006/041997 | 4/2006 |
| WO | WO 2007/030379 | 3/2007 |
| WO | WO 2008/006150 | 1/2008 |
| WO | WO 2008/010604 | 1/2008 |
| WO | WO 2009/052607 | 4/2009 |
| WO | WO 2009/120951 | 10/2009 |
| WO | WO 2009/141777 | 11/2009 |
| WO | WO 2010/020919 | 2/2010 |
| WO | WO 2010/105053 | 9/2010 |
| WO | WO 2011/082420 | 7/2011 |
| WO | WO 2011/113070 | 9/2011 |
| WO | WO 2011/123848 | 10/2011 |
| WO | WO 2012/141999 | 10/2012 |
| WO | WO 2013/026999 | 2/2013 |
| WO | WO 2013/044226 | 3/2013 |
| WO | WO 2013/155193 | 10/2013 |
| WO | WO 2014/036577 | 3/2014 |
| WO | WO 2015/112095 | 7/2015 |
| WO | WO 2015/168720 | 11/2015 |
| WO | WO 2016/025438 | 2/2016 |
| WO | WO 2016/030752 | 3/2016 |
| WO | WO 2016/058032 | 4/2016 |
| WO | WO-2016073777 A1 | 5/2016 |
| WO | WO 2016/100218 | 6/2016 |
| WO | WO 2016/109744 | 7/2016 |
| WO | WO 2016/110564 | 7/2016 |
| WO | WO 2016/187136 | 11/2016 |
| WO | WO 2016/205872 | 12/2016 |
| WO | WO 2016/205881 | 12/2016 |
| WO | WO 2017/021006 | 2/2017 |
| WO | WO 2017/021965 | 2/2017 |
| WO | WO 2017/033058 | 3/2017 |
| WO | WO 2017/037479 | 3/2017 |
| WO | WO 2017/041014 | 3/2017 |
| WO | WO 2017/041385 A1 | 3/2017 |
| WO | WO 2017/041386 | 3/2017 |
| WO | WO 2017/041387 | 3/2017 |
| WO | WO 2017/119996 | 7/2017 |
| WO | WO 2017/205728 | 11/2017 |
| WO | WO 2017/214188 | 12/2017 |
| WO | WO 2018/035612 | 3/2018 |
| WO | WO 2018/060417 | 4/2018 |
| WO | WO 2018/064569 | 4/2018 |
| WO | WO 2018/115461 | 6/2018 |
| WO | WO 2018/144938 | 8/2018 |
| WO | WO 2018/144941 | 8/2018 |
| WO | WO 2018/144943 | 8/2018 |
| WO | WO 2018/144946 | 8/2018 |
| WO | WO 2018/162728 | 9/2018 |
| WO | WO 2018/162732 | 9/2018 |
| WO | WO 2018/162735 | 9/2018 |
| WO | WO 2018/162736 | 9/2018 |
| WO | WO 2018/185138 | 10/2018 |
| WO | WO 2018/189265 | 10/2018 |
| WO | WO 2018/209090 | 11/2018 |
| WO | WO 2018/210692 | 11/2018 |
| WO | WO 2018/210693 | 11/2018 |
| WO | WO 2018/211458 | 11/2018 |
| WO | WO 2018/234443 | 12/2018 |
| WO | WO 2019/020550 | 1/2019 |
| WO | WO 2019/020551 | 1/2019 |
| WO | WO 2019/020666 | 1/2019 |
| WO | WO 2019/030384 | 2/2019 |
| WO | WO 2019/048624 | 3/2019 |
| WO | WO 2019/048626 | 3/2019 |
| WO | WO 2019/048638 | 3/2019 |
| WO | WO 2019/063481 | 4/2019 |
| WO | WO 2019/063488 | 4/2019 |
| WO | WO 2019/067264 | 4/2019 |
| WO | WO 2019/072531 | 4/2019 |
| WO | WO 2019/076967 | 4/2019 |
| WO | WO 2019/096828 | 5/2019 |
| WO | WO 2019/140441 | 7/2019 |
| WO | WO 2019/140444 | 7/2019 |
| WO | WO-2019/140448 | 7/2019 |
| WO | WO 2019/140449 | 7/2019 |

OTHER PUBLICATIONS

Aubakir, B. et al., "Vital Sign Monitoring Utilizing Eulerian Video Magnification and Thermography", 2016 38th Annual International Conference of the IEEE Engineering in Medicine and Biology Society, Aug. 16, 2016, pp. 3527-3530, in 4 pages.

Bandodkar, A. et al., "Battery-free, skin-interfaced microfluidic/electronic systems for simultaneous electrochemical, colorimetric, and volumetric analysis of sweat", Science Advances, vol. 5(1), Jan. 18, 2019, in 16 pages. URL: http://advances.sciencemag.org/content/5/1/eaav3294.

(56) References Cited

OTHER PUBLICATIONS

Cauwe, M. et al., "Technology development for a low-cost, roll-to-roll chip embedding solution based on PET foils", 18th European Microelectronics and Packaging Conference (EMPC), IEEE, Sep. 12, 2011, in 6 pages.
Farooqui, M. et al., "Low Cost Inkjet Printed Smart Bandage for Wireless Monitoring of Chronic Wounds", Scientific Reports, vol. 6, Jun. 29, 2016, in 14 pages.
Geng, Y. et al., "A Hybrid Low Power Biopatch for Body Surface Potential Measurement", IEEE Journal of Biomedical and Health Informatics, vol. 17(3), May 1, 2013, XP011506375.
Great Britain Office Action and Search Report, re GB Application No. 1703771.4, dated Aug. 29, 2017.
Great Britain Office Action and Search Report, re GB Application No. 1703772.2, dated Aug. 11, 2017.
Iannetta, R.A. et al., "Successful case histories of polymer based circuitry on flexible film substrates", Electro/94 International Conference Proceedings Combined Volumes, IEEE, May 10-12, 1994, XP010149465.
Jinto, G. et al., "Reliability of Plastic-Encapsulated Electronic Components in Supersaturated Steam Environments", IEEE Transactions on Components, Packaging, and Manufacturing Technology, vol. 5, No. 10, Oct. 2015, in 9 pages.
Lu, B. et al., "A study of the autofluorescence of parylene materials for [mu]TAS applications", Lab on Chip, vol. 10, No. 14, Jul. 2010, pp. 1826-1834, in 9 pages.
McLeod, A. et al., "Motion Magnification for Endoscopic Surgery", Progress in Biomedical Optics and Imaging, SPIE—International Society for Optical Engineering, Mar. 12, 2014, vol. 9036, in 8 pages.
Mostafalu, P. et al., "Wireless Flexible Smart Bandage for Continuous Monitoring of Wound Oxygenation", IEEE Transactions on Biomedical Circuits and Systems, vol. 9, No. 5, Oct. 2015, pp. 670-677, in 8 pages.
Narusawa, H., "The corona discharge causes short destruction that had bad influence on a power switching circuit", Adphox Corporation, Jan. 1, 2009, in 12 pages, URL: http://www.adphox.co.jp/keisokuki/ke-english-corona/CORONA_DISCHARGE_EN.pdf.
Raviglione, A. et al., "Real-Time Smart Textile-Based System to Monitor Pressure Offloading of Diabetic Foot Ulcers", Journal of Diabetes Science and Technology, vol. 11, Sep. 2017, in 5 pages.
Rose, D. et al., "Adhesive RFID Sensor Patch for Monitoring of Sweat Electrolytes", IEEE Transactions on Biomedical Engineering, vol. 62(6), Jun. 2015 (first published Nov. 11, 2015), in 9 pages.
Wakita, J. et al., "Variations in Optical Absorption and Fluorescence Spectra for Polyimide Thin Films Caused by Structural Isomerism", J. Photopolym. Sci. Technol. Jan. 1, 2003, in 1 page.
Willis, B., "Conformal Coating Inspection & Coating Faults", Vision Engineering, Jul. 21, 2016, in 35 pages. URL: http://www.visioneng.com/wp-content/uploads/2017/11/Confirmal-Coating-Inspection-and-Defects.21JUL16.pdf.
Willis, B., "Guide to Conformal Coating & Cleaning Defects Contents", Mar. 1, 2014, in 31 pages. URL: http://coatingguide.smartgroup.org/Files%20pdf/Coating%20Defects%20V2%2014March2014.pdf.
International Search Report and Written Opinion, re PCT Application No. PCT/EP2018/055945, dated Jul. 4, 2018.
International Preliminary Report on Patentability for Application No. PCT/EP2018/055945, dated Sep. 19, 2019, 11 pages.
Mehmood N., et al., "Applications of Modern Sensors and Wireless Technology in Effective Wound Management: Modern Sensors and Wireless Technology," Journal of Biomedical Materials Research Part B, vol. 102, May 1, 2014, XP055739544, pp. 885-895.

\* cited by examiner

APPARATUS AND METHOD FOR IMAGING BLOOD IN A TARGET REGION OF TISSUE

CROSS-REFERENCE TO RELATED APPLICATIONS

[0001] This application is a U.S. national stage application of International Patent Application No. PCT/EP2018/0055945, filed Mar. 9, 2018, which claims the benefit of GB Application No. 1703771.4, filed Mar. 9, 2017, and GB Application No. 1703772.2, filed Mar. 9, 2017, the disclosure of each of which is hereby incorporated by reference in its entirety.

This disclosure relates to apparatus for imaging blood within a target region of tissue and a corresponding method of imaging blood within a target region of tissue.

Wound healing is natural process performed by the human body in response to injury. The amount of time taken for a wound to heal is dependent on many different factors which include the human body's ability to heal itself and any treatments that are applied to the wound to accelerate wound healing. Understanding the healing status of a wound and being able to monitor the healing process helps to inform decisions on further treatment of the wound and can also assist in the development of future wound therapies.

One factor that is known to be associated with wound healing is the amount of blood supplied to blood vessels within tissue at or near a wound. The process of supplying blood to blood vessels within tissue is known as blood perfusion. Oxygen and nutrients carried by blood within wounded tissue are essential for wound healing and so the amount of oxygenated blood within tissue is known to correlate well with wound healing. Conventional techniques for determining the presence of blood within skin tissue include near-infrared imaging to determine oxygen saturation of blood vessels within tissue at or near a wound.

Typically, such techniques require specialised equipment that is both bulky and expensive. Techniques for imaging blood within tissue can be hampered by reflection of illuminating light by the upper surface of the tissue.

It is an aim of the present disclosure to at least partly mitigate the above-mentioned problems.

It is an aim of certain embodiments of the present disclosure to provide a means for imaging blood within tissue that can utilise a light source that provides illumination using visible light having a broad spectral range.

It is an aim of certain embodiments of the present disclosure to mitigate the effect of illuminating light which does not penetrate tissue on images obtained of blood within the tissue.

It is an aim of certain embodiments of the present disclosure to provide a means for imaging blood within tissue such that blood perfusion within the tissue can be assessed.

According to some embodiments, there is provided apparatus for imaging blood within a target region of tissue, comprising: an imaging device configured to output image data associated with light received by the imaging device having a first spectral range and configured to output image data associated with light received by the imaging device having a second spectral range, wherein the absorptivity by blood of light having the first spectral range is less than the absorptivity by blood of light having the second spectral range; and a controller or controlling element configured to capture the image data associated with light received by the imaging device having the first spectral range and image data associated with light received by the imaging device having the second spectral range contemporaneously and to process the captured image data associated with light having the first spectral range and the captured image data associated with light having the second spectral range to generate compound image data associated with an amount of blood within the target region of tissue.

The imaging device may comprise an imaging sensor comprising a plurality of sensor elements, wherein each sensing element is configured to output data associated with the amount of light received by the sensing element at the first spectral range and to output data associated with the amount of light received by the sensing element at the second spectral range.

The plurality of sensor elements may be arranged in a two-dimensional array. The imaging sensor may comprise a digital imaging sensor. The digital imaging sensor may comprise a complementary metal-oxide semiconductor image sensor or a charge-couple device imaging sensor.

The controlling element may be configured to record a first value associated with the amount of light received by each sensing element at the first spectral range and a second value associated with the amount of light received by each sensing element at the second spectral range.

The controlling element may be further configured to generate a compound value associated with each sensing element based on the first value and the second value. The compound value may be a difference between the first value and the second value. The controlling element may be configured to apply a scaling factor to the first value and/or second value when generating the compound value.

The apparatus may further comprise a digital display unit, wherein the controlling element is configured to display a digital image comprising a plurality of pixels on the display, wherein each pixel is associated with at least one of the sensing elements and each pixel has a value based on the compound value associated with each respective sensing element.

The digital image may have a predefined brightness and/or colour scale based on which the compound values for each sensing element are represented.

The first spectral range may correspond to a spectral range associated with red light. The second spectral range may correspond to a spectral range associated with green light.

The apparatus may further comprise a light source configured to provide illuminating light having the first spectral range and to provide illuminating light having the second spectral range.

The light source may be configured to provide illuminating light having a spectral range which encompasses the first spectral range and the second spectral range. The light source may comprise at least one light emitting diode.

According to some embodiments, there is provided a method of imaging blood within a target region of tissue comprising the steps of: capturing image data associated with at least a portion of a target region of tissue at a first spectral range; capturing image data associated with at least the portion of a target region of tissue at a second spectral range, wherein the absorptivity by blood of light having the first spectral range is less than the absorptivity by blood of light having the second spectral range, wherein the image data associated with at least a portion of a target region of tissue at a first spectral range and the image data associated with at least the portion of a target region of tissue at a second spectral range are captured contemporaneously; and processing the image data captured at the first spectral range and the image data captured at the second spectral range to generate compound image data associated with an amount of blood within the target tissue.

The step of capturing image data at the first spectral range and the step of capturing image data at the second spectral range may comprise capturing image data using an imaging sensor comprising a plurality of sensor elements to capture image data associated with the amount of light received by each sensing element at each of the first spectral range and the second spectral range.

The step of processing the image data captured at the first spectral range and the image data captured at the second spectral range may comprise the step of comparing a first value associated with the amount of light received by each sensing element at the first spectral range and a second value associated with the amount of light received by each sensing element at the second spectral range.

The step of processing the image data captured at the first spectral range and the image data captured at the second spectral range may comprise the step of generating a compound value associated with each sensing element based on the first value and the second value. The compound value may be a difference between the first value and the second value.

The method may further comprise the step of applying a scaling factor to the first value and/or second value when generating the compound value.

The method may further comprise the step of at least one of displaying, storing and transmitting the compound image data for analysis.

The method may further comprise the step of generating digital image having a predefined brightness and/or colour scale based on which the compound values for each sensing element are represented.

The first spectral range may correspond to a spectral range associated with red light. The second spectral range may correspond to a spectral range associated with green light.

The method may further comprise the step of illuminating the target region of tissue using a light source which provides illuminating light having first spectral range and the second spectral range. The illuminating light may have a spectral range which encompasses the first spectral range and the second spectral range. The light source may comprise at least one light emitting diode.

Certain embodiments of the present disclosure allow for images to be obtained of a target region of tissue that provide an indication of the amount and/or distribution and/or concentration of blood within the skin tissue. Certain embodiments of the present disclosure allow for images to be obtained using digital imaging sensors.

Certain embodiments of the present disclosure allow for images to be obtained using digital imaging sensors configured to produce image data having at least two components associated with different spectral ranges.

Certain embodiments of the present disclosure allow for images to be generated by combining image data having at least two components associated with different spectra ranges.

According to some embodiments, there is provided apparatus for imaging blood within a target region of tissue, comprising: an imaging device configured to output image data associated with light received by the imaging device having a first spectral range and configured to output image data associated with light received by the imaging device having a second spectral range, wherein the absorptivity by blood of light having the first spectral range is less than the absorptivity by blood of light having the second spectral range; and a controller or controlling element configured to capture the image data associated with light received by the imaging device having the first spectral range and image data associated with light received by the imaging device having the second spectral range contemporaneously and to process the captured image data associated with light having the first spectral range and the captured image data associated with light having the second spectral range to generate compound image data associated with an amount of blood within the target region of tissue, wherein the first spectral range corresponds to a spectral range associated with red light.

According to some embodiments, there is provided apparatus for imaging blood within a target region of tissue, comprising: a light source configured to provide illuminating light having a first spectral range and to provide illuminating light having a second spectral range; an imaging device configured to output image data associated with light received by the imaging device having the first spectral range and configured to output image data associated with light received by the imaging device having the second spectral range, wherein the absorptivity by blood of light having the first spectral range is less than the absorptivity by blood of light having the second spectral range; and a controller or controlling element configured to capture the image data associated with light received by the imaging device having the first spectral range and image data associated with light received by the imaging device having the second spectral range contemporaneously and to process the captured image data associated with light having the first spectral range and the captured image data associated with light having the second spectral range to generate compound image data associated with an amount of blood within the target region of tissue.

According to some embodiments, there is provided a method of imaging blood within a target region of tissue comprising the steps of: capturing image data associated with at least a portion of a target region of tissue at a first spectral range; capturing image data associated with at least the portion of a target region of tissue at a second spectral range, wherein the absorptivity by blood of light having the first spectral range is less than the absorptivity by blood of light having the second spectral range, wherein the image data associated with at least a portion of a target region of tissue at a first spectral range and the image data associated with at least the portion of a target region of tissue at a second spectral range are captured contemporaneously; and processing the image data captured at the first spectral range and the image data captured at the second spectral range to generate compound image data associated with an amount of blood within the target tissue, wherein the second spectral range corresponds to a spectral range associated with green light.

According to some embodiments, there is provided a method of imaging blood within a target region of tissue comprising the steps of: illuminating a target region of tissue using a light source which provides illuminating light having a first spectral range and a second spectral range, wherein the illuminating light has a spectral range which encompasses the first spectral range and the second spectral range; capturing image data associated with at least a portion of a target region of tissue at the first spectral range; capturing image data associated with at least the portion of a target region of tissue at the second spectral range, wherein the absorptivity by blood of light having the first spectral range is less than the absorptivity by blood of light having the second spectral range, wherein the image data associated with at least a portion of a target region of tissue at a first spectral range and the image data associated with at least the portion of a target region of tissue at a second spectral range are captured contemporaneously; and processing the image data captured at the first spectral range and the image data captured at the second spectral range to generate compound image data associated with an amount of blood within the target tissue.

According to some embodiments, there is provided apparatus for imaging blood within a target region of tissue, comprising: a light source configured to illuminate at least a portion of a target region of tissue with linearly polarised light having at least a first spectral range and a second spectral range, wherein the absorptivity by blood of light having the first spectral range is less than the absorptivity by blood of light having the second spectral range; an imaging system having an imaging sensor configured to capture an image of at least a portion of the target region of tissue illuminated by the linearly polarised light; and a first linearly polarising filter arranged in front of the imaging device such that, in use, the polarising filter is disposed between the imaging device and the target region of tissue, wherein the first linearly polarising filter is arranged to block polarised illuminating light reflected by the target region of tissue.

The first linearly polarising filter may be arranged to polarise light in a plane which is orthogonal to the plane of polarisation of the illuminating light.

The light source may comprise a light emitter configured to emit unpolarised light and a second linearly polarising filter disposed in front of the light emitter. The light emitter may comprise at least one light emitting diode.

The second linearly polarising filter may be arranged in a cross-polarised configuration with respect to the first polarising filter such that light polarised by the second linearly polarising filter which remains polarised after being reflected by the target region of skin tissue is blocked by the first linearly polarising filter.

The first and second linearly polarising filters may be arranged such that the plane of polarisation of the first linearly polarising filter is at an angle of 90 degrees to the plane of polarisation of the second linearly polarising filter. The light source may be configured to illuminate the portion of the target region of tissue with visible light.

The first spectral range may correspond to a spectral range associated with red light and the second spectral range corresponds to a spectral range associated with green light.

The light source may comprise a diffuser arranged to provide diffused illuminating light.

The apparatus may be a smartphone.

According to some embodiments, there is provided a method of imaging blood within a target region of tissue, comprising the steps: illuminating a target region of tissue using linearly polarised light having at least a first spectral range and a second spectral range, such that the linearly polarised light is scattered and/or reflected by the target region of tissue, wherein the absorptivity by blood of light having the first spectral range is less than the absorptivity by blood of light having the second spectral range; arranging an imaging system comprising an imaging sensor such that the imaging sensor is arranged to receive light scattered and/or reflected by the target region of tissue; disposing a linearly polarising filter between the target region of tissue and the imaging sensor such that scattered light which has been depolarised by the target region of tissue is transmitted by the linearly polarising filter and reflected light which remains polarised is blocked by the linearly polarising filter; and using the imaging system to capture at least one image of at least a portion of the target region of tissue using light which has been transmitted by the linearly polarising filter.

The linearly polarising filter may be arranged such that the plane of polarisation of the linearly polarising filter is orthogonal to the plane of polarisation of the illuminating light.

The step of illuminating a target region of tissue using linearly polarised light may comprise the step of using a light emitter configured to emit unpolarised light to emit light and disposing a second linearly polarising filter in front of the emitter to polarise the illuminating light. The target region of tissue may be illuminated with visible light.

The visible light may comprise a first spectral range that corresponds to a spectral range associated with red light and a second spectral range that corresponds to a spectral range associated with green light. The linearly polarised light may be diffused light.

According to some embodiments, there is provided a method of imaging blood within a target region of tissue, comprising the steps: illuminating a target region of tissue using linearly polarised light having at least a first spectral range and a second spectral range, such that the linearly polarised light is scattered and/or reflected by the target region of tissue, wherein the absorptivity by blood of light having the first spectral range is less than the absorptivity by blood of light having the second spectral range; transmitting by a linearly polarising filter disposed between the target region of tissue and the imaging sensor scattered light which has been depolarised by the target region of tissue and blocking by the linearly polarising filter reflected light which remains polarised; receiving with an imaging sensor light scattered and/or reflected by the target region of tissue; and capturing at least one image of at least a portion of the target region of tissue using light which has been transmitted by the linearly polarising filter.

The linearly polarising filter may be arranged such that the plane of polarisation of the linearly polarising filter is orthogonal to the plane of polarisation of the illuminating light.

The step of illuminating a target region of tissue using linearly polarised light may comprise the step of using a light emitter configured to emit unpolarised light to emit light and disposing a second linearly polarising filter in front of the emitter to polarise the illuminating light. The target region of tissue may be illuminated with visible light.

The visible light may comprise a first spectral range that corresponds to a spectral range associated with red light and a second spectral range that corresponds to a spectral range associated with green light. The linearly polarised light may be diffused light.

Certain embodiments of the present disclosure allow for images of blood within tissue to be obtained that are not adversely affected by light which is reflected by the tissue without penetrating the tissue.

Embodiments of the present disclosure will now be described, by way of example only, with reference to the accompanying drawings in which.

Figure 1:
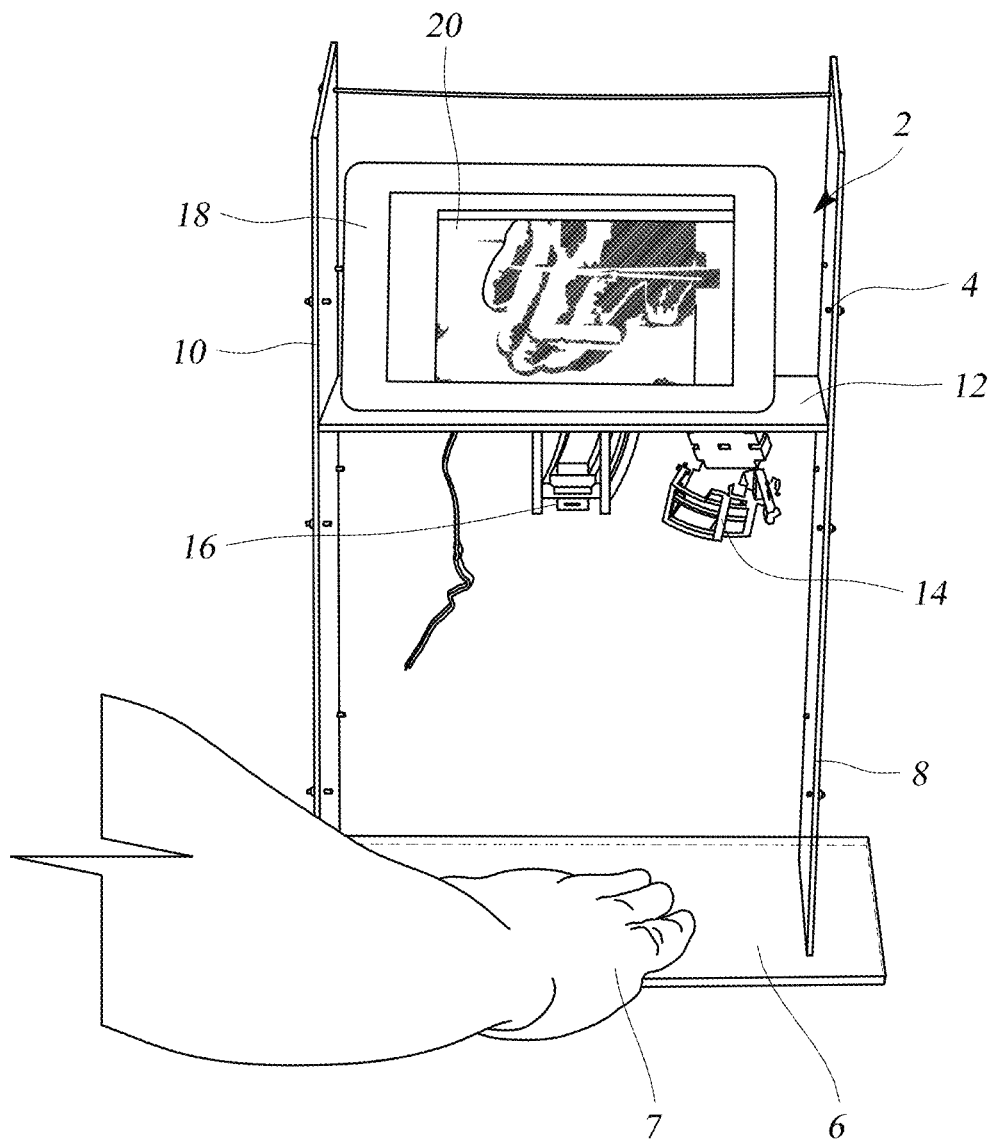
FIG. 1 shows an imaging apparatus for imaging a target region of tissue.

FIG. 1 shows an apparatus 2 for imaging blood vessels within a target region of tissue being used to investigate distribution of blood within tissue at the back of a portion of a person's hand 7. The apparatus 2 could, of course, be used to image other regions of a person's body or portions of an animal's body such as a region of a torso or a leg or an arm, for example.

The apparatus 2 comprises a support structure in the form of a support frame 4 having a base 6 on which the hand 7 is placed, walls 8, 10 which extend upwardly from the base 6 and an equipment support platform 12. The support platform 12 extends horizontally from one wall 8 to the other wall 10 and is located above the base 6 and spaced away from the base 6 by a suitable distance. In the embodiment shown, the support platform 12 is spaced from the base 6 by 30 cm. The support platform 12 may be spaced from the base 6 by between 5 cm and 100 cm, such as between 20 cm and 50 cm in accordance with requirements such as a requirement to keep a target region of tissue within a focal range of a camera module, as described below.

A light source 14 is secured to the support platform 12 and arranged to illuminate the back of the hand 7 placed on the base 6 below. A camera module 16 is also secured to the support platform 12 and arranged to capture images of the back of the hand 7 placed on the base 6 below. The support frame 4 therefore holds the light source 14 and the camera module 16 in a fixed special relationship with respect to each other and the base 6. A display unit 18 for processing and displaying images captured by the camera module 16 is secured to the support platform 12. In the embodiment show, the display unit 18 comprises a portable device having an integrated screen 20. The display unit 18 may be a tablet device, smart phone, laptop, computer or the like.

Figure 2:
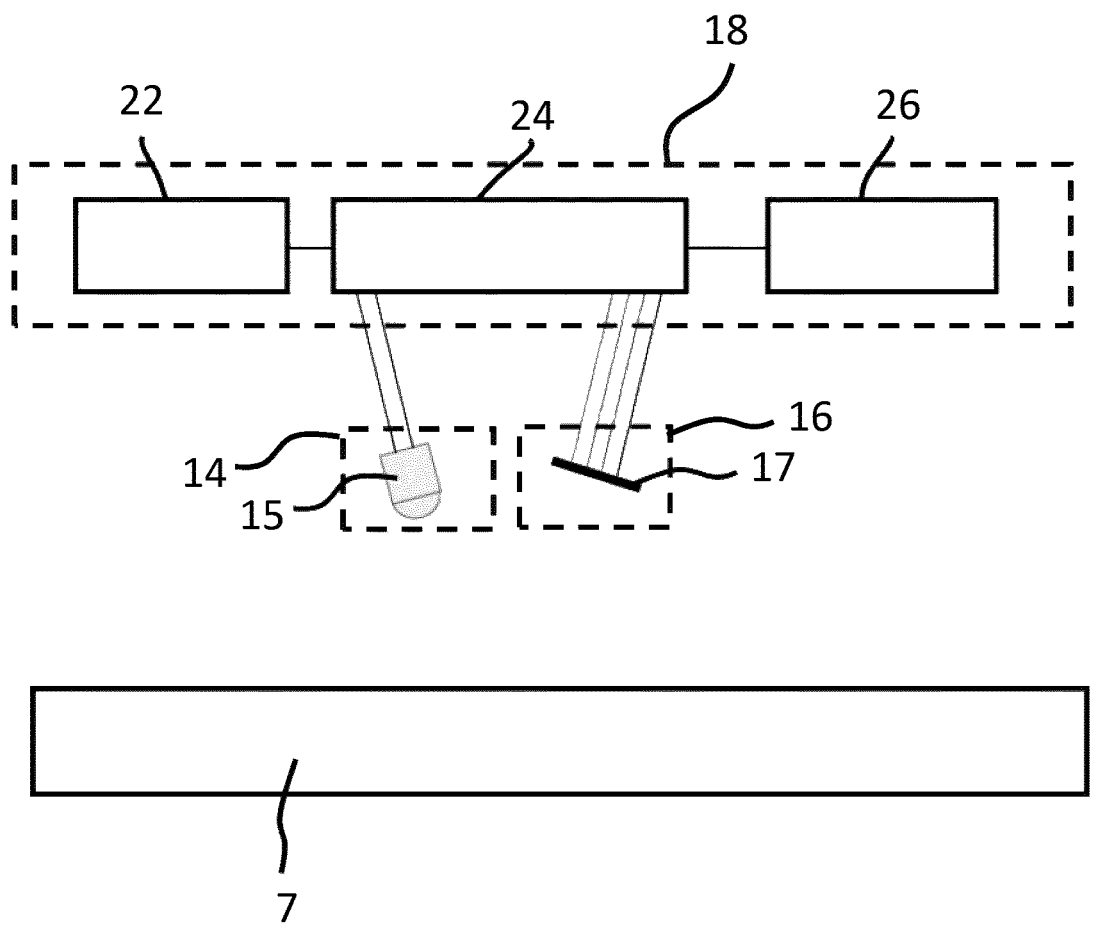
FIG. 2 is a schematic representation of key components of the imaging apparatus shown in FIG. 1.

FIG. 2 is a schematic representation of components of the apparatus 2 shown in FIG. 1. Components of the display unit 18 are enclosed by broken lines. The display unit 18 comprises a power source in the form of a battery 22, a controller or processor 24 and an output device 26 which is configured to display an output from the processor 24 on the screen 20 of the display unit 8. The processor 24 is configured to control the light source 14 and to process image data from the camera module 16. In other embodiments, other power sources may be used such as a mains power supply or the like.

In the embodiment shown, the light source 14 is a high-intensity light source in the form of an LED torch. The LED torch comprises a plurality of LEDs 15 which are configured to emit white light having a broad spectral range. For example, each LED may be configured to emit light having spectral range of wavelengths between 380 nm and 770 nm.

The camera module 16 comprises a digital imaging sensor 17 having a two-dimensional array of discrete sensing elements. Each sensing element is configured to produce an output having three separate components including: a component associated with the amount of red light received at the sensing element; a component associated with the amount of green light received at the sensing element; and a component associated with the amount of blue light received at the sensing element.

In the embodiment shown, each sensing element comprises three separate identical sensors. Each sensing element has a respective filter configured to transmit light within a predefined spectral range associated with one of red, green and blue light respectively.

Such digital imaging sensors are commonly used in the field of digital photography. In the embodiment shown, the digital imaging sensor is a complementary metal-oxide semiconductor (CMOS) digital imaging sensor. The sensor is a Sony™ IMX219 sensor configured to produce image data for generating a 3296 by 2512 pixel image.

Figure 3:
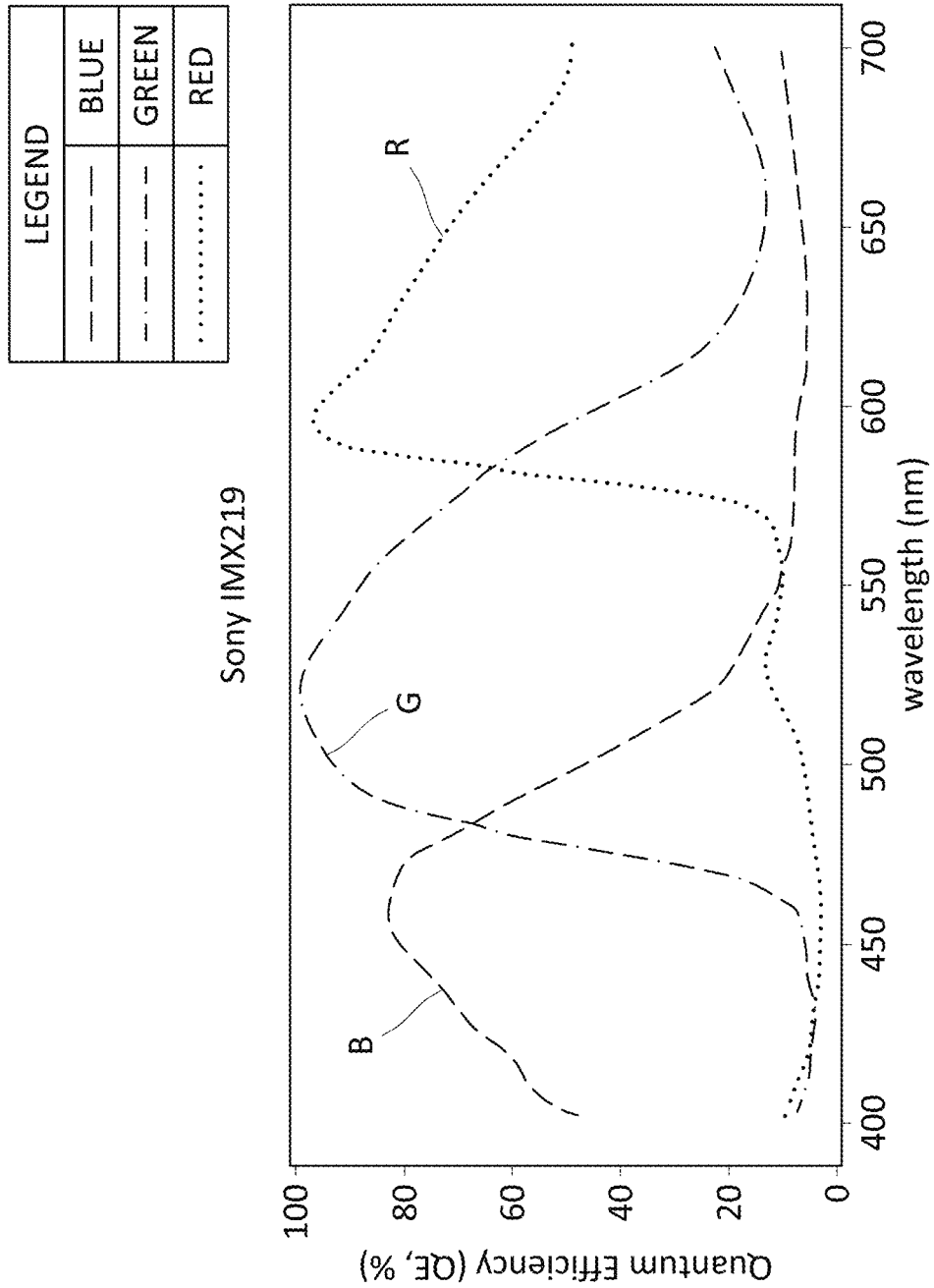
FIG. 3 is a graphical illustration of spectral response curves for a sensor used in the apparatus shown in FIG. 1.

The spectral response curves for each of the component outputs of the digital imaging sensor 17 is shown in FIG. 3.

The spectral response curve associated with the amount of blue light received at each sensing element is shown by response curve B. The response curve has a peak response for blue light within the spectral range 400 nm and 500 nm. The spectral response curve associated with the amount of green light received at each sensing element is shown by response curve G. The response curve has a peak response for green light within the spectral range 520 nm and 580 nm. The spectral response curve associated with the amount of red light received at the sensing element is shown by response curve R. The response curve has a peak response for red light within the spectral range 590 nm and 750 nm.

The imaging sensor 17 is therefore configured to produce output components associated with the amount of blue, green and red light received at each sensing element which can be processed to generate an image comprising an array of pixels in which each pixel is associated with a respective sensor element. Images can therefore be produced in which each pixel has a blue, green or red value that corresponds to the amount of blue, green and red light received at each sensing element. Other sensors having suitable response curves such as a charge coupled devices (CCD) or the like could of course be utilised.

Figure 4:
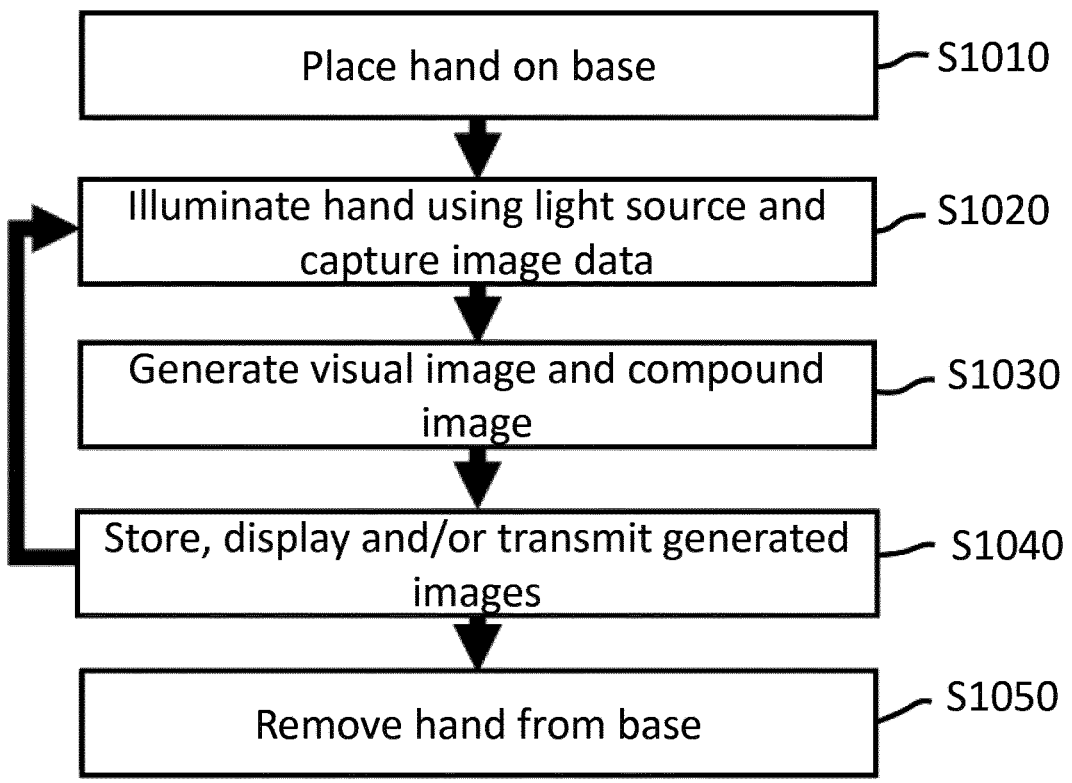
FIG. 4 is a flow chart of a method of imaging a target region of tissue using the apparatus shown in FIG. 1.

A flow chart illustrating a method of imaging blood within a target region of tissue in order to determine the distribution of blood within the tissue is shown in FIG. 4.

At step S1010, a hand 7 is placed with the palm facing upward on the base 6 of the support frame 4 below the light source 14 and the camera module 16.

At step S1020, the light source 14 is activated by the processor 24 to illuminate the region of the hand 7 in view of the camera module 16. While the hand is illuminated, the camera module 16 is controlled by the processor 24 to produce image data associated with a target region of tissue of the hand 7 which is within view of the camera module 16 and illuminated by the light source 14. In particular, the digital imaging sensor 17 of the camera module 16 is controlled to produce image data for each of the sensing elements forming the array of sensing elements. The image data for each sensing element has blue, green and red components, as described above.

At step S1030, the processor 24 determines a value for each of the blue, green and red components based on the received image data. In particular, the processor 24 generates a red value $I_R$ and a green value $I_G$ and a blue value $I_B$ for each sensing element. The red value $I_R$ is associated with the amount of red light received by the sensing element. The green value $I_G$ is associated with the amount of green light received by the same sensing element. The blue value $I_B$ is associated with the amount of blue light received by the same sensing element. The values are then used to generate a visual digital image and a compound digital image of the target region of tissue. The step of generating a visual digital image is optional. Each image comprises an array of pixels in which the location of each pixel corresponds to the location of a corresponding sensing element of the imaging sensor 17.

Figure 6B:
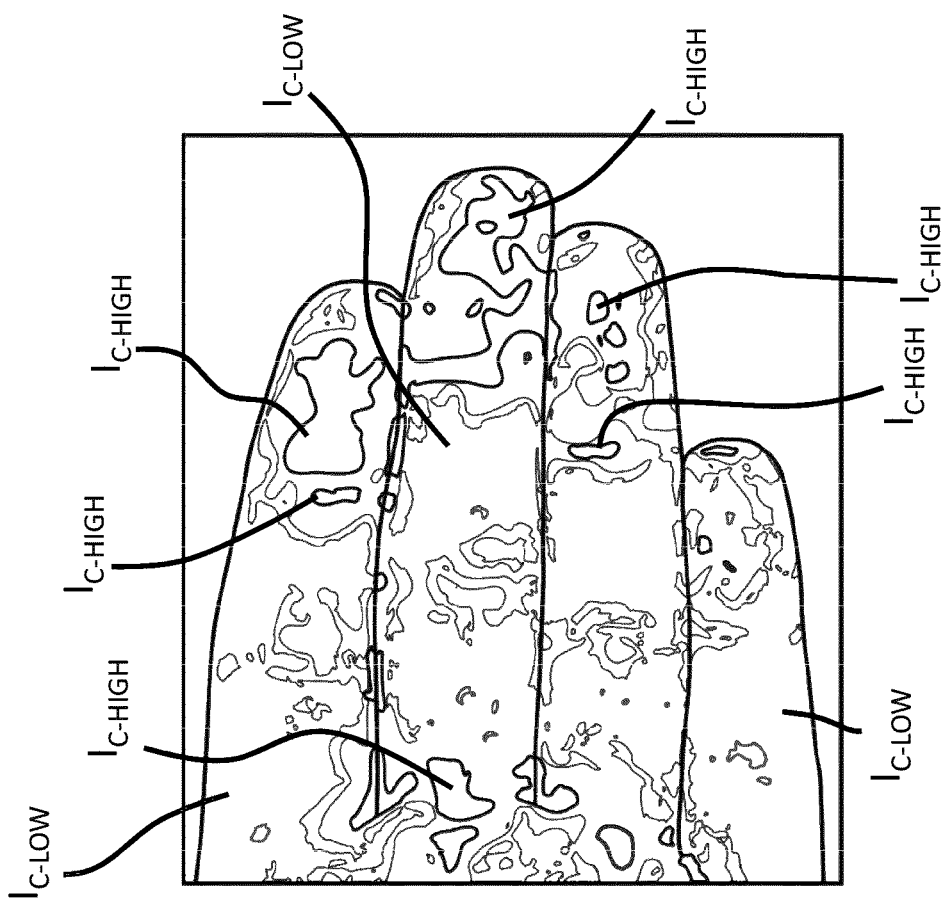
FIG. 6B is an illustrative example of a further image generated by the apparatus shown in FIG. 1.
Figure 6A:
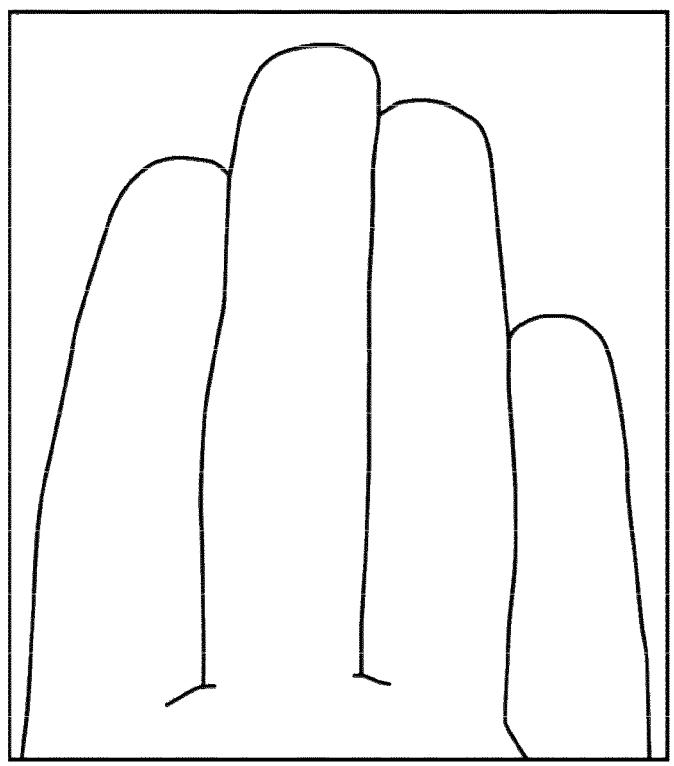
FIG. 6A is an illustrative example of an image generated by the apparatus shown in FIG. 1.

The processor 24 generates the visual digital image, as shown in FIG. 6A, using all three components to produce an image corresponding to that which is seen by the naked eye. The image is displayed on the screen 20 of the display unit 18 by the output device 26. The first image allows the target region of tissue to be inspected by a clinician to determine that the hand 7 is positioned correctly and that there are no anomalies that may affect analysis.

In order to generate the compound digital image, the processor 24 generates a compound value $I_C$ for each sensing element which corresponds to a respective pixel of the compound digital image.

A compound value $I_C$ for each pixel is generated by subtracting the green value $I_G$ from the red value $I_R$. In order to compensate for differences in the amount of red and green light that is emitted by the light source 14, or to compensate for differences in the sensitivity of the imaging sensor 17 to red and green light, a scaling factor 'a' is applied to the green value $I_G$. The value of 'a' may also set in accordance with other subjective factors related to representation and interpretation of the second image. The value of 'a' may be in the range 0.01 to 100, such as in the range 0.1 to 10 and may be in the range 1 to 5, such as 1. The compound value $I_C$ is therefore calculated as follows:

$$I_C = I_R - a \cdot I_G$$

The magnitude of the compound value $I_C$ provides an indication of the local distribution of blood within the target region of tissue associated with the pixel. This is because haemoglobin within blood absorbs green light much better than red light and so the amount of green light received at a sensing element is heavily dependent on the amount of blood within skin tissue whereas the amount of red light received at a sensing element is not.

Figure 5:
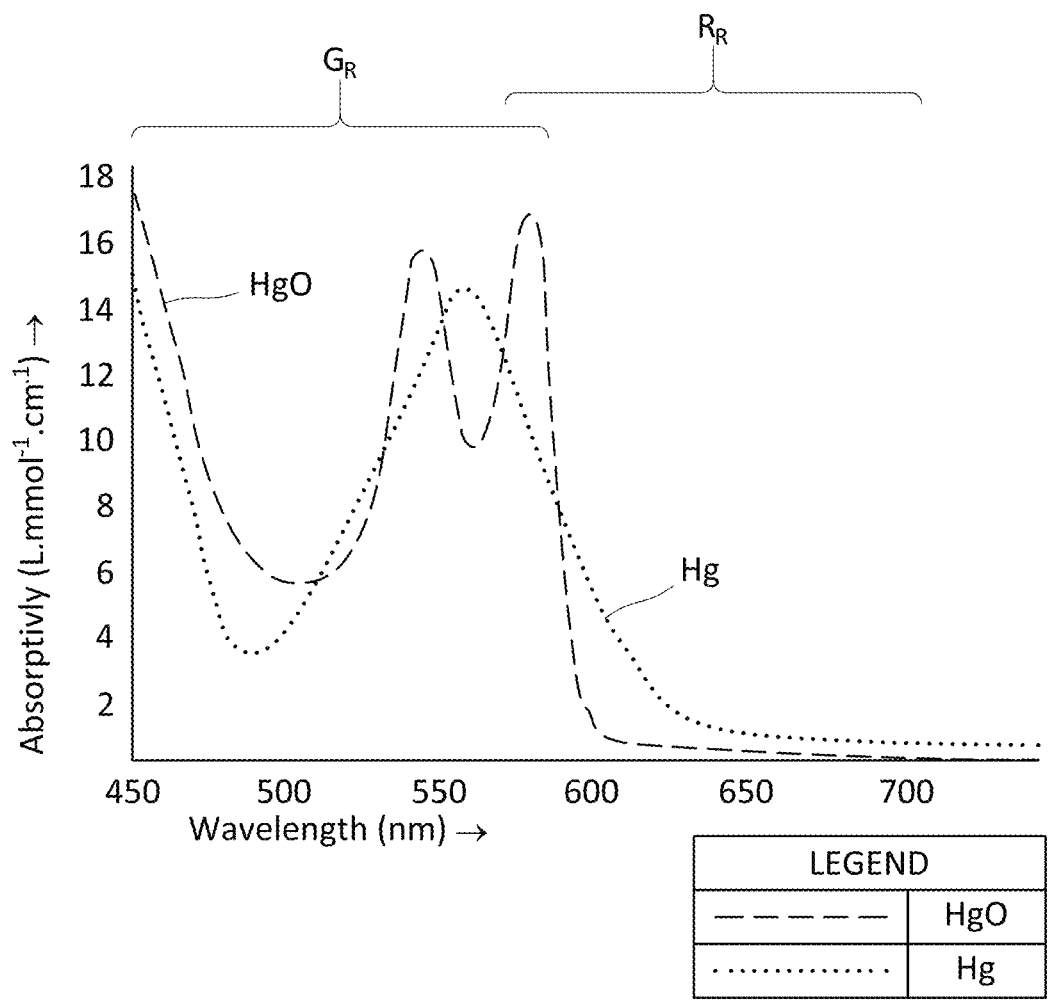
FIG. 5 is graphical illustration showing absorptivity of light by haemoglobin for different wavelengths.

To aid further explanation, FIG. 5 shows the spectral absorption by haemoglobin and haemoglobin species of light having wavelengths between 450 nm and 750 nm (as described at http://www.derangedphysiology.com/main/core-topics-intensive-care/arterial-blood-gas-interpretation/Chapter%203.0.1/absorption-spectroscopy-haemoglobin-species, which is incorporated herein by reference in its entirety).

Compared against the spectral response curves shown in FIG. 3, it can be seen that haemoglobin and the species oxygenated haemoglobin absorb more green light corresponding to the spectral range of the response curve G than they absorb red light corresponding to the spectral range of the response curve R. Consequently, the amount of green light absorbed at the target region of tissue is highly dependent on the amount of blood within the tissue. Conversely, the amount of red light absorbed at the target region of tissue has a much lower dependency on the amount of blood within the tissue.

The approximate ranges of the response curves G and R are superimposed on FIG. 5 as $G_R$ and $R_R$, respectively. Although there is some overlap of the ranges $G_R$ and $R_R$, it will be appreciated that overall proportion of green light absorbed by the haemoglobin within the tissue will be greater than the proportion of red light absorbed.

The green value $I_G$ for each pixel is proportional to the amount of green light detected by the imaging sensor 17 and so is inversely proportional to the amount of light absorbed. Therefore, a low green value $I_G$, and by implication a high compound value $I_C$, is associated with a large amount of blood within the region of tissue. The compound value $I_C$ therefore provides a reliable indicator of the amount of blood within tissue depicted by an associated pixel in the compound image.

In contrast, the skin tissue itself absorbs green and red light having spectral ranges corresponding to those shown in FIG. 3 substantially equally and so the value of $I_C$ is relatively unaffected by the nature of the skin tissue surrounding blood vessels.

In the embodiment shown, the compound value $I_C$ is converted for each pixel using a suitable scale, for example, based on brightness and/or a colour range to produce the second image, as shown in FIG. 6B. Areas having a greater amount (higher concentration) of blood within the tissue (i.e. comprising pixels having a relatively high $I_{C\text{-}HIGH}$ value) and areas having a lesser amount (lower concentration) of blood within the tissue (i.e. comprising pixels having a relatively low $I_{C\text{-}LOW}$ value) are delineated by contour lines within the image.

Although spectral ranges associated with high and low amounts of absorptivity by haemoglobin and oxygenated haemoglobin are utilised in the present embodiment to evaluate the concentration of blood within tissue, other spectral ranges could be selected in addition to, or as an alternative, that correspond to high and low amounts of absorptivity for other compounds that may be found within tissue and other compounds that may be found within blood.

It will be appreciated that, in the present embodiment, the light source 14 is configured to emit light having at least one wavelength, or range of wavelengths, which is both well absorbed by blood and which falls within the range of the response curve of the imaging sensor 17 associated with green light and at least one wavelength, or range of wavelengths, which is less well absorbed by blood and which falls within the range of the response curve of the imaging sensor 17 associated with red light.

Figure 7:
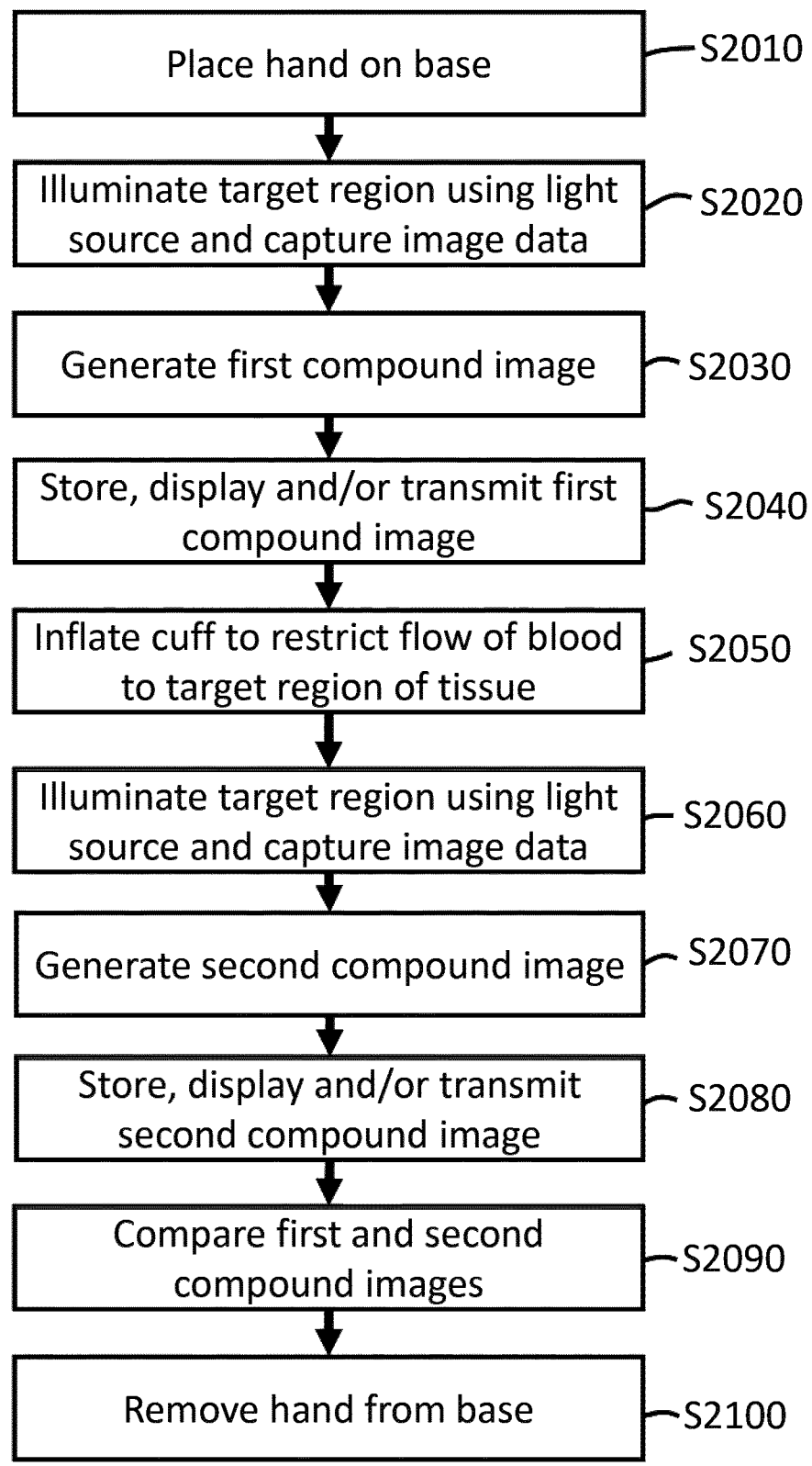
FIG. 7 is a flow chart of further method of imaging a target region of tissue using the apparatus shown in FIG. 1.

FIG. 7 shows a flow chart illustrating a further method of using the apparatus 2 shown in FIG. 1 to monitor changes in blood perfusion within skin tissue. The apparatus 2 is used in conjunction with a restriction device in the form of an inflatable cuff (not shown) such as an Omron M3 Comfort Automatic Upper Arm Blood Pressure Monitor. In this example, the inflatable cuff is wrapped around a person's upper arm of the hand that is to be inspected.

Figure 8A:
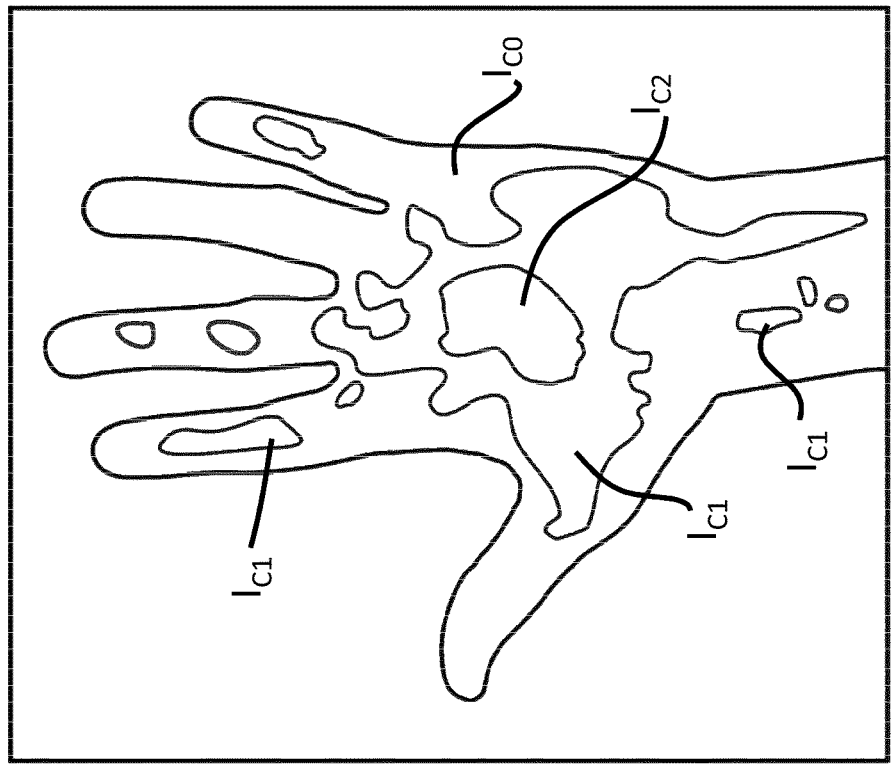
FIG. 8A is an illustrative example of an image generated by the method shown in FIG. 7.

At step S2010, a hand is placed on the base 6 of the apparatus 2. At step S2020, the light source 14 is activated to illuminate a target region of tissue of the hand. At step 2030, a first compound image is generated using components of the output of the camera module 16 as described above in connection with the process step S1030. A visual image may also be generated, as described in step S1030. However, such a step is optional and omitted in this instance. At step S2040, a first compound image is stored, transmitted or displayed on the integrated display unit 18. FIG. 8A shows a first compound image in which the hand is relatively well perfused. In this image, a scale having bands $I_{C0}$, $I_{C1}$, $I_{C2}$, $I_{C3}$, $I_{C4}$ for different $I_C$ values is used to distinguish between areas having lowest $I_C$ values $I_{C0}$ (i.e. low blood concentration) and areas having highest $I_C$ values $I_{C4}$ (i.e. high blood concentration). Areas in which high and low concentrations of blood are present are therefore easy to identify within the image.

At step 2050, the inflatable cuff is inflated in order to restrict blood flow to the target region of tissue. After a suitable period of time has elapsed in which it can be expected that the restriction has reduced blood flow within the target region of tissue, the target region is illuminated again at step S2060, image data is captured by the camera module 16 and a second compound image is generated at step S2070. The suitable period of time may be at least 1 second or at least 2 seconds or at least 5 seconds. The light source 14 may be deactivated between capture of the first and second compound images or else remain activated throughout steps S2020 to S2060.

Figure 8B:
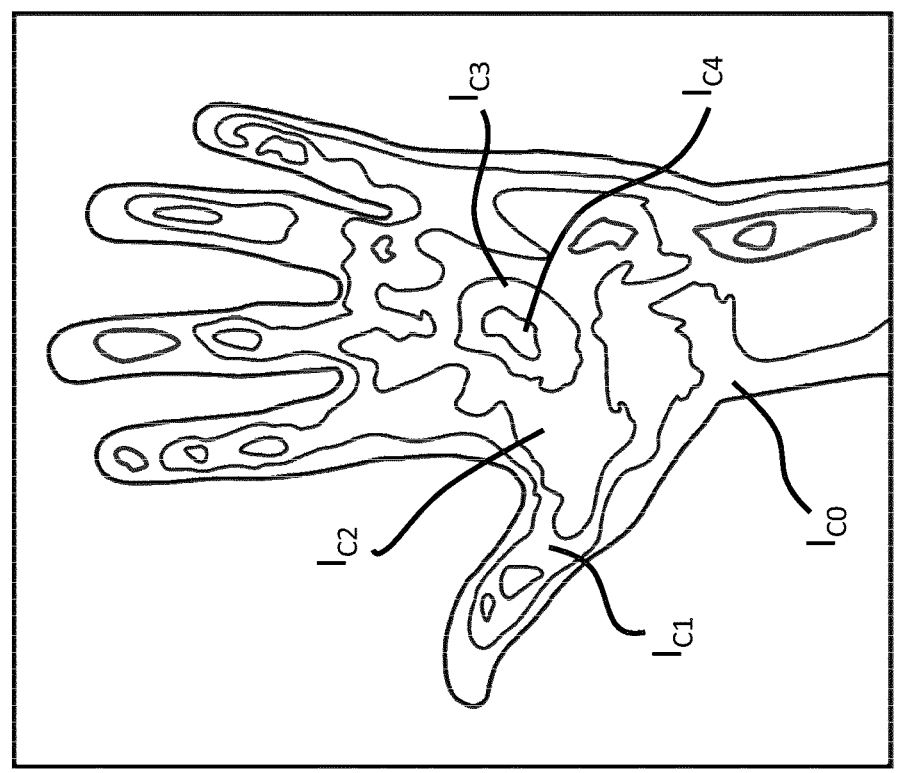
FIG. 8B is an illustrative example of a further image method generated by the method shown in FIG. 7.

FIG. 8B shows a second compound image in which the hand 7 is poorly perfused following restriction by the inflatable cuff. There are, therefore, relatively few areas of the image in which indicate that high concentrations of blood are present in the target region of tissue. The highest compound value $I_C$ in this image is $I_{C2}$ compared with $I_{C4}$ in the first image which indicates that much lower concentrations of blood are present.

Comparison of first and second compound images, for example by a clinician, enables a qualitative assessment of blood perfusion to the target region of tissue. For example, if the inflation pressure of the cuff is known, the amount of blood perfusion in the second compound image in comparison the first compound image may be used to determine whether blood flow to the tissue is within normal bounds.

In further embodiments, restriction of blood flow to the target region of tissue may be done by a tourniquet or pressing against a vessel supplying blood to the tissue or by pressing against the target region of tissue itself.

Figure 9:
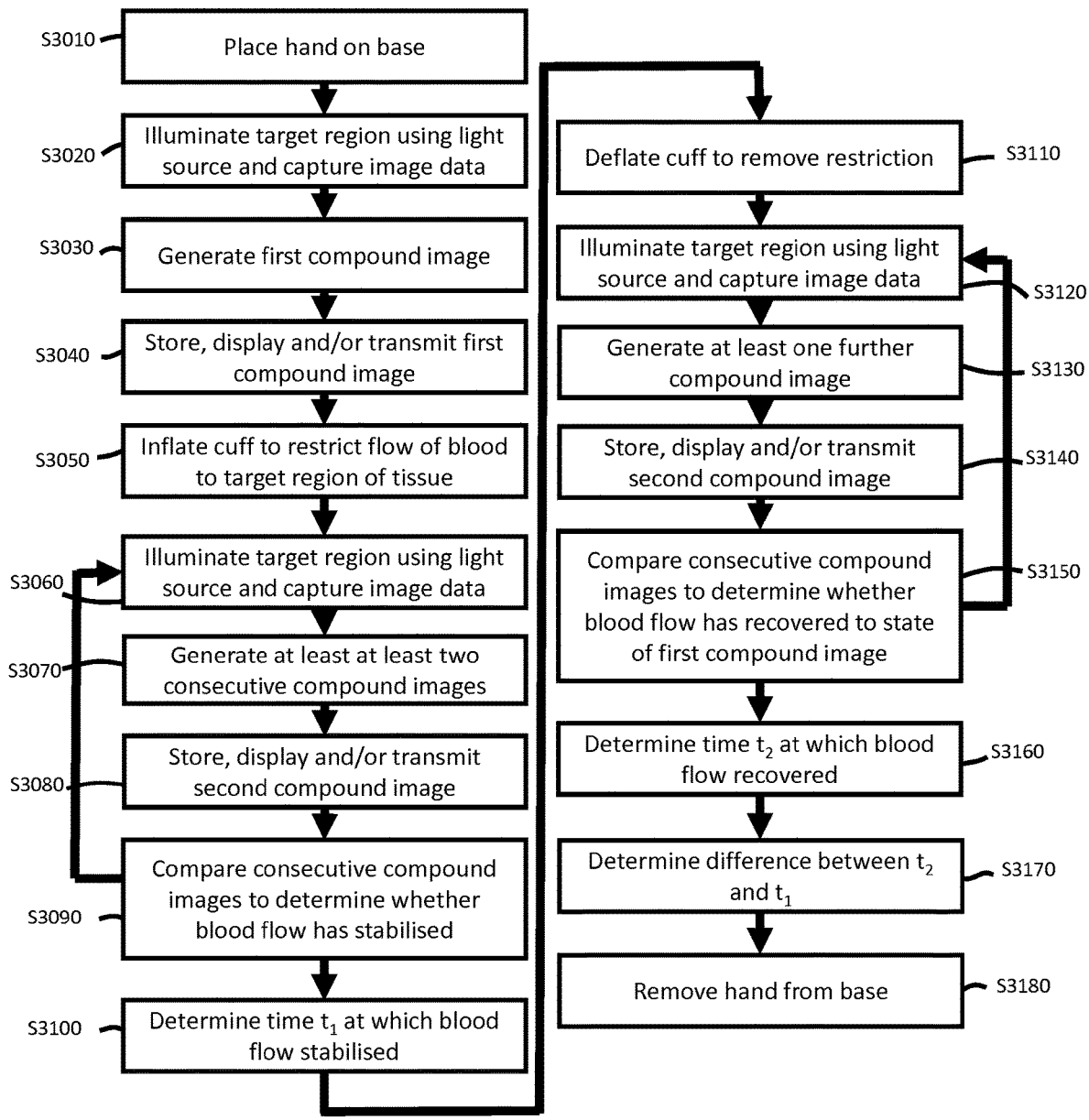
FIG. 9 is a flow chart of a further method of imaging a target region of tissue using the apparatus shown in FIG. 1.

FIG. 9 shows a variation of the method shown in FIG. 7.

Figure 10C:
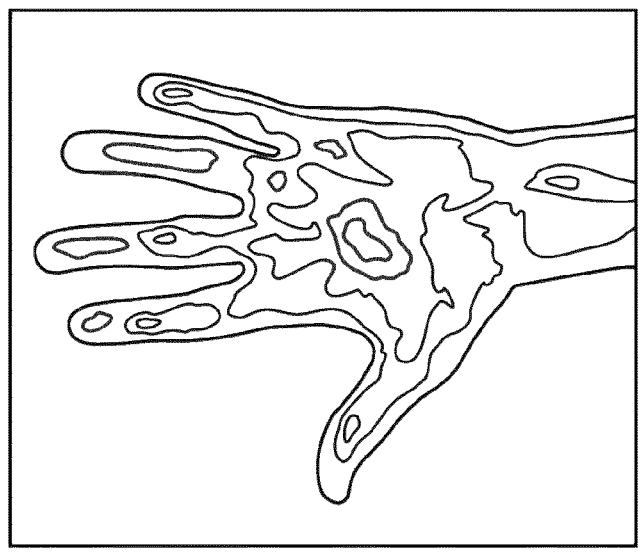
FIG. 10C is an illustrative example of an image generated using the method shown in FIG. 9.
Figure 10B:
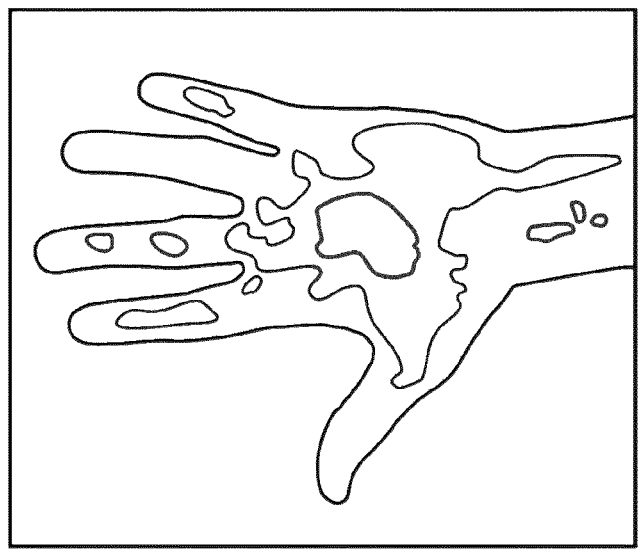
FIG. 10B is an illustrative example of an image generated using the method shown in FIG. 9.
Figure 10A:
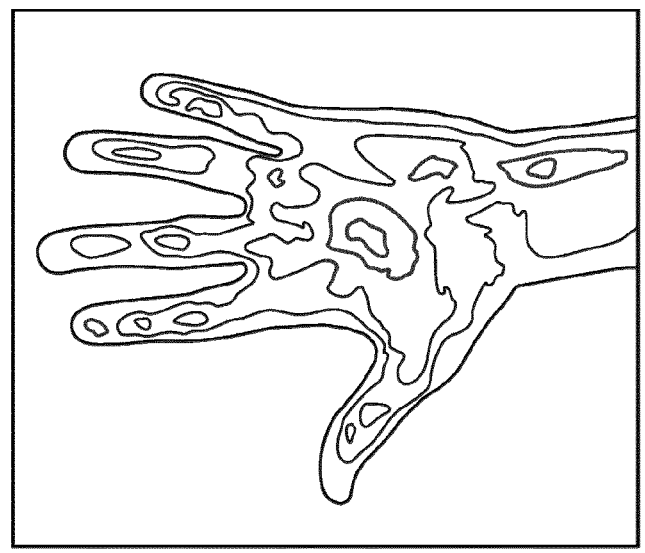
FIG. 10A is an illustrative example of an image generated using the method shown in FIG. 9.

At steps S3010 to S3050, which are the same as steps S2010 to S2050, a first compound image of a target region of tissue is obtained. An example of a first compound image is shown in FIG. 10A.

At step S3060, the target region of tissue is illuminated and image data is captured such that at step S3070, at least two consecutive compound images of the target region of tissue are captured after the cuff has been inflated. The consecutive images are stored, displayed or transmitted at step S3080 for analysis. At step S3090, the consecutive images are compared to determine whether the flow of blood within the target region has stabilised. The consecutive images may be compared visually by a clinician or automatically using image analysis software. If blood flow has not stabilised, steps S3060 to S3090 are repeated until it is determined that flow of blood within the target region of tissue is stable. An example of a compound image of the target region of tissue after it has been determined that the flow of blood within the tissue has stabilise is shown in FIG. 10B.

At step S3100, the time $t_1$ at which blood flow has stabilised is recorded and the restriction removed immediately at step S3110 by deflation of the cuff. Steps S3120 to S3140 (which correspond to steps S3020 to S3040) are then followed to obtain a further compound image of the target region of tissue. At step S3150, the further compound image is compared against the first compound image to determine whether the distribution of blood within the tissue at the target region, and hence the flow of blood within the tissue, has returned/recovered to the original state prior to restriction of the blood flow. The comparison may once again be made visually by a clinician or automatically using suitable image analysis software. If distribution of blood has not returned to the original state, steps S3120 to S3150 are repeated. Once it is determined that the distribution of blood has returned, or has substantially returned, to its original state, the time $t_2$ at which it does so is recorded. An example of a compound image obtained showing the distribution of blood within the target region of tissue once it has returned to its original state is shown in FIG. 10C.

It will be appreciated that small movements of the tissue, hysteresis within the tissue and other variations will make it unlikely that blood flow within the tissue will return to the original state exactly. Therefore, suitable parameters may be used such as a proportion of the pixels of the compound image having a compound value $I_C$ which is within a predetermined percentage of the first compound image or a return to an average $I_C$ value for a selection of pixels of the image may be sufficient to determine that the distribution of blood has returned to the original state. The difference between time $t_2$ and time $t_1$ can then be calculated to determine a recovery time $t_R$ that provides an indication of the quality of blood perfusion at the target region.

A variant of the method shown in FIG. 9 has steps S3060 to S3100 omitted. Instead, a predetermined period of time is allowed to lapsed after inflation of the cuff which is sufficient to assume that blood flow has stabilised. The target region can then be imaged once the blood flow is known to have stabilised.

Figure 11:
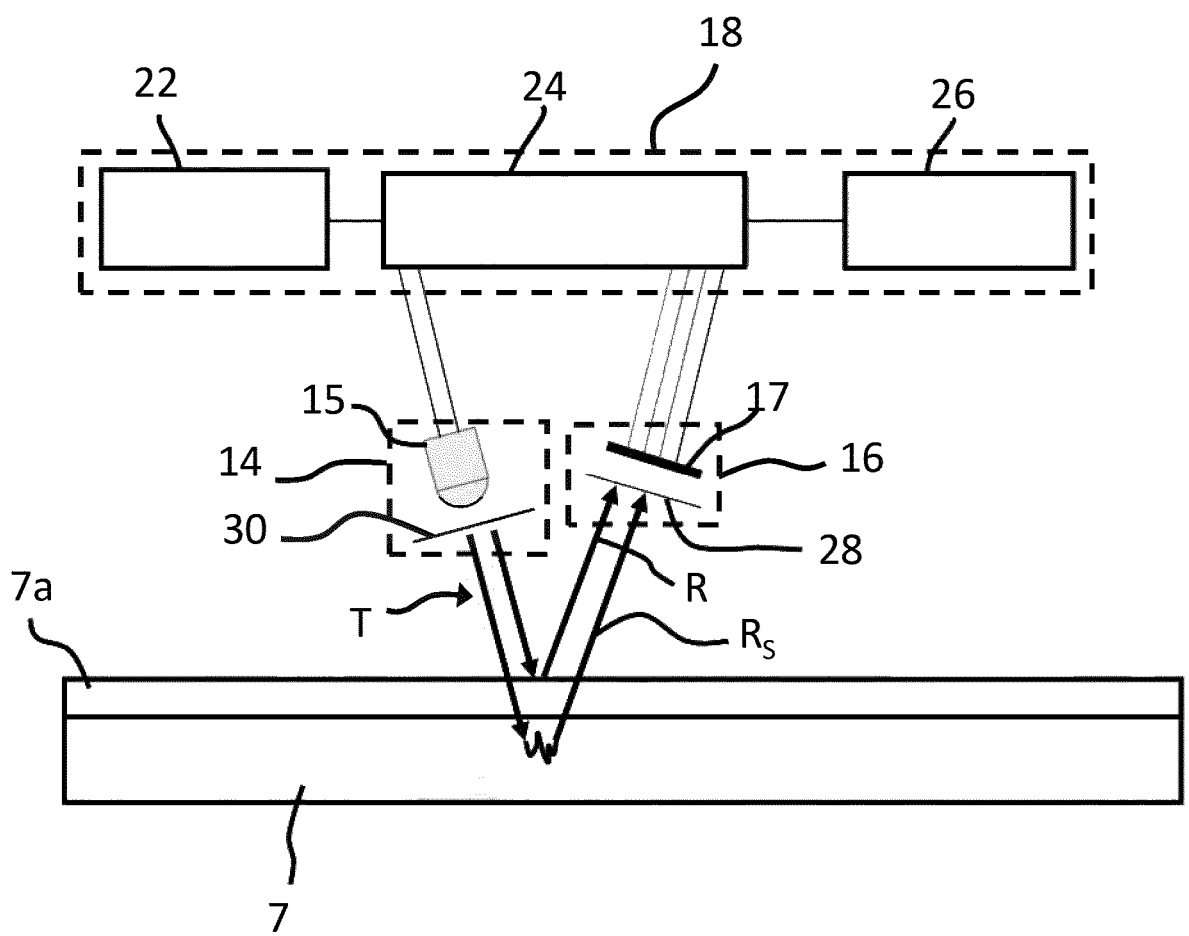
FIG. 11 is a schematic presentation of apparatus for imaging a target region of skin tissue.

FIG. 11 shows a variation of the apparatus shown in FIG. 1 further comprising first and second linear polarising filters 28, 30. The first linear polarising filter 28 mounted in front of the camera module 16 and the second linear polarising filter 30 is mounted in front of the light source 14 so that light emitted by the light source 14 is polarised before reaching the target region of tissue of the hand 7 and light reflected by the tissue towards the camera module 16 is polarised before it reaches the camera module 16.

The first and second linear polarising filters are 28, 30 are arranged in a cross-polarised configuration so that light polarised by the second linear polarising filter 30 which has not been de-polarised before reaching the first linear polarising filter 28 will be blocked by the first linear polarising filter 28 and so prevented from reaching the imaging sensor 17 in the camera module 16. The polarising plane of the first linear polarising filter 28 is at 90 degrees to the polarising plane of the second linear polarising filter 30. The first and second linear polarising filters 28, 30 are set up in a cross-polarised configuration by placing a piece of flat aluminium foil (not shown) on the base 6 in the region at which the hand 7 is placed. The light source 14 is then used to illuminate the aluminium foil and images are captured of the illuminated portion of the aluminium foil. The first linear polarising filter 28 is then rotated with respect to the second linear polarising filter 30 until the light intensity of the captured images is at a minimum. At this orientation, the two polarising filters 28, 30 are considered to be in a cross-polarised configuration.

Only light T transmitted by the light source 14 and polarised by the second polarising filter 30 which is subsequently depolarised by the target region of tissue, for example on account of scattering events within the tissue, passes through the first linear polarising filter 28 to the camera module 16. Consequently, only light $R_S$ which has penetrated the epidermis 7*a* of the skin tissue which undergoes multiple scattering events, and so has had an increased likelihood of being absorbed by blood vessels within the skin tissue, is used to generate an image of the target region. Light R which has been reflected without penetrating the skin tissue, and so which would provide an unreliable indication of the amount of blood within the skin tissue is prevented from reaching the camera module 16. The embodiment, when used to capture images using the methods outlined above, improves the quality and reliability of the images generated.

In some embodiments, a dedicated light source may be unnecessary since ambient light may be sufficient.

Camera modules comprising CCD or CMOS imaging sensors have been described with respect to the embodiments above. Other imaging sensors may be used that are suitable for detecting the spectral content of light and producing a digital image comprising a plurality of pixels in which each pixel can have a value that corresponds a spectral content of light received by the sensor at a corresponding portion of the sensor. Other imaging sensors having other suitable response curves may also be used.

Image data or images generated using image data can be processed or post-processed to enhance features of interest. For example, the brightness of images can be adjusted or contrast enhanced or colour adjusted or noise filter techniques or the like can be applied. Other imaging processing techniques may be used to highlight features of interest within the images.

Various light sources can be used for illumination. Light emitting diodes or a single diode may be used in accordance with the embodiments described above. Surface mounted diodes, which are compact, widely available, inexpensive, reliable, produce high-intensity light, have lower power consumption and are easy to integrate, may be used. Other light sources such as lasers, laser diodes, digital light projectors (DLPs), organic light emitting diodes (OLED) or incandescent light sources or the like may be used. The light source may be a broad-band or white light source such as the light source used in the embodiments described above, but may be a light source capable of illuminating the target region at two or more wavelengths, such as two monochromatic light sources, two laser diodes of different wavelengths, a multi-coloured LED or the like. Two light sources may be used, neither of which has an emission spectra extending over a region of overlap of response curves for the imaging sensor in which there is a significant response for each response curve. In an arrangement which comprises two light sources, the spectral range of one light source may be different from the spectral range of the other light source. For example, red and green LEDs could be used as respective light sources. An imaging sensor could be used which does not discriminate between the two spectral ranges and the light sources may be sequentially pulsed (i.e. activated and deactivated alternately) in order to obtain images at each of the respective spectral ranges. Diffuser of lens arrangements may be used to provide a reasonably uniform illumination across a region of interest or to focus light on particular areas of interest.

The light source, camera module and display unit may be incorporated into a portable hand-held device having a single housing in which the components are housed. For example, a hand-held digital camera unit having an integrated flash unit could be configured to generate images in accordance with the imaging methods described above.

Figure 12:
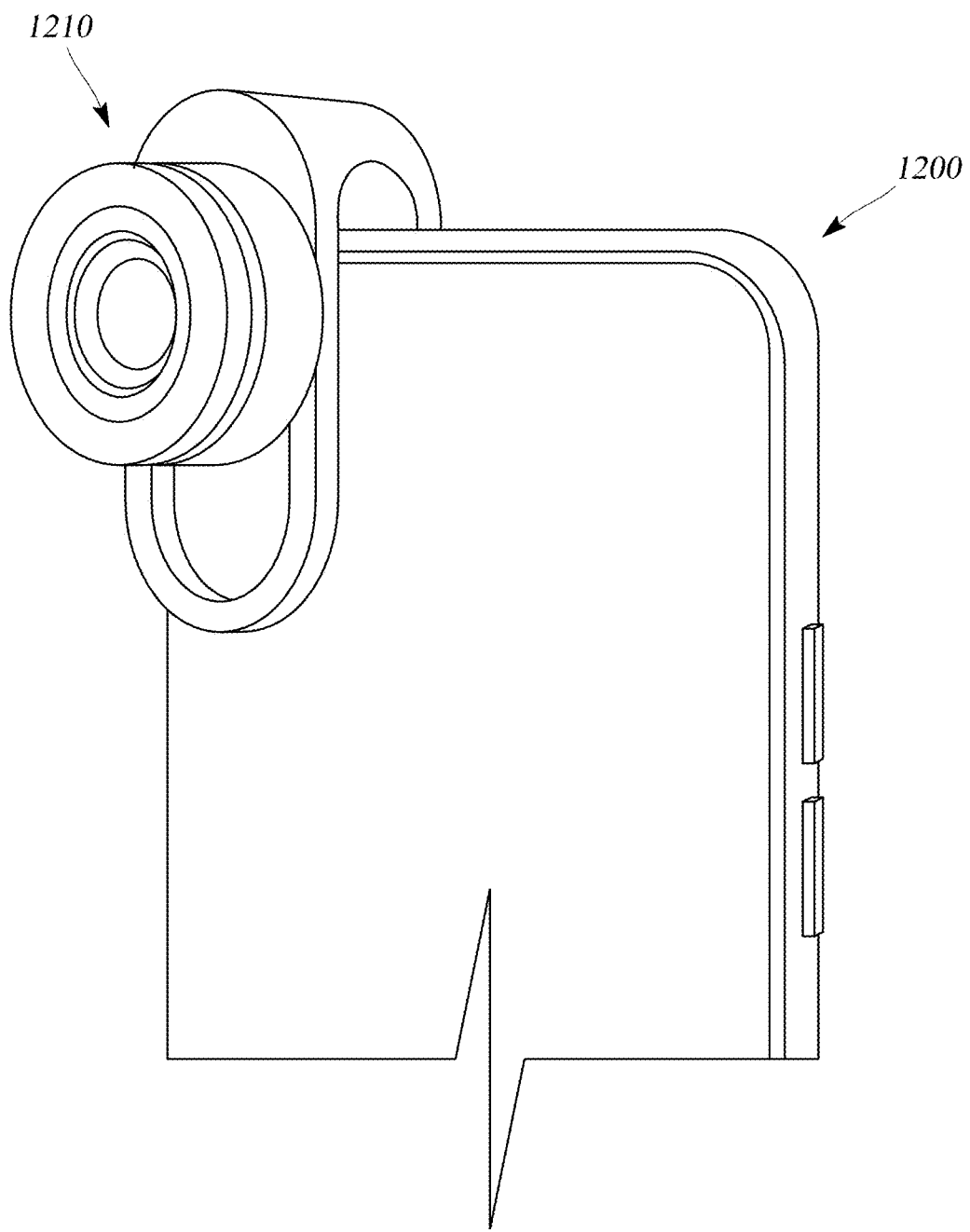
FIG. 12 is presentation of another apparatus for imaging a target region of skin tissue.

In some embodiments, the portable hand-held device can be a smartphone, tablet, or the like with an integrated camera and a flash. For example, as illustrated in FIG. 12, the hand-held device can be a smartphone 1200. The camera can be utilised to capture one or more images or videos. For instance, one or more images can be captured using standard, burst capture, such as IPHONE™ live photo capture. Capturing one or more images or videos can permit processing of the differential in absorption substantially in real time or offline.

One or more polarising filters (as described herein) can be positioned over the flash. The flash can be turned on for the duration of the image or video capture. An orthogonal polarising filter (whose polarising plane can be at 90 degrees to polarising plane(s) of the one or more filters positioned over the flash as described herein) can be positioned over an image lens of the camera. In some cases, the one or more filters positioned over the flash and the orthogonal filter positioned over the image lens are connected to be in cross-polarised configuration as described herein. The one or more filters positioned over the flash can be tinted to prioritise only the frequencies of interest as described herein.

Alternatively or additionally, a lens, such as macro lens 1210, can be used over the image lens of the camera. Alternatively or additionally, a separate illumination source can be used. In any of the embodiments described herein, Eulerian amplification techniques can be used in the analysis, as described in U.S. Provisional Patent Application Nos. 62/506,524, filed May 15, 2017 and 62/506,551, filed May 15, 2017, each of which is incorporated herein by reference in its entirety. Eulerian magnification can, for example, amplify variations in absorption due to the pulse providing bursts of blood.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

In the drawings like reference numerals refer to like parts.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the disclosure are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The disclosure is not restricted to any details of any foregoing embodiments. The disclosure extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference in their entireties.

The invention claimed is:

1. Apparatus for imaging blood within a target region of tissue, comprising:
    a light source configured to illuminate at least a portion of the target region of tissue with linearly polarised light where blood flow has been restricted, the linearly polarised light having at least a first spectral range and a second spectral range, wherein the absorptivity by blood of light having the first spectral range is less than the absorptivity by blood of light having the second spectral range;
    an imaging system having an imaging sensor configured to capture an image of at least a portion of the target region of tissue illuminated by the linearly polarised light while blood flow is restored to the target region of tissue; and
    a first linearly polarising filter arranged in front of the imaging sensor such that, in use, the first linearly polarising filter is disposed between the imaging sensor and the target region of tissue, wherein the first linearly polarising filter is arranged to block polarised illuminating light reflected by the target region of tissue.

2. The apparatus of claim 1, wherein the first linearly polarising filter is arranged to polarise light in a plane which is orthogonal to the plane of polarisation of the linearly polarised light.

3. The apparatus of claim 1, wherein the light source comprises a light emitter configured to emit unpolarised light and a second linearly polarising filter disposed in front of the light emitter.

4. The apparatus of claim 3, wherein the light emitter comprises at least one light emitting diode.

5. The apparatus of claim 3, wherein the second linearly polarising filter is arranged in a cross-polarised configuration with respect to the first linearly polarising filter such that light polarised by the second linearly polarising filter which remains polarised after being reflected by the target region of tissue is blocked by the first linearly polarising filter.

6. The apparatus of claim 5, wherein the first and second linearly polarising filters are arranged such that the plane of polarisation of the first linearly polarising filter is at an angle of 90 degrees to the plane of polarisation of the second linearly polarising filter.

7. The apparatus of claim 1, wherein the light source is configured to illuminate the portion of the target region of tissue with visible light.

8. The apparatus of claim 7, wherein the first spectral range corresponds to a spectral range associated with red light and the second spectral range corresponds to a spectral range associated with green light.

9. The apparatus of claim 1, wherein the light source comprises a diffuser arranged to provide diffused illuminating light.

10. The apparatus of claim 1, wherein the apparatus comprises a smartphone.

11. A method of imaging blood within a target region of tissue, comprising the steps:
    restricting blood flow to the target region of tissue;
    after removing the restriction, illuminating the target region of tissue using linearly polarised light having at least a first spectral range and a second spectral range, such that the linearly polarised light is scattered and/or reflected by the target region of tissue, wherein the absorptivity by blood of light having the first spectral range is less than the absorptivity by blood of light having the second spectral range;
    arranging an imaging system comprising an imaging sensor such that the imaging sensor is arranged to receive light scattered and/or reflected by the target region of tissue;
    disposing a linearly polarising filter between the target region of tissue and the imaging sensor such that scattered light which has been depolarised by the target region of tissue is transmitted by the linearly polarising filter and reflected light which remains polarised is blocked by the linearly polarising filter; and
    using the imaging system to capture at least one image of at least a portion of the target region of tissue using light which has been transmitted by the linearly polarising filter.

12. The method of claim 11, wherein the linearly polarising filter is arranged such that the plane of polarisation of the linearly polarising filter is orthogonal to the plane of polarisation of the linearly polarised light.

13. The method of claim 12, wherein the step of illuminating the target region of tissue using linearly polarised light comprises the step of using a light emitter configured to emit unpolarised light to emit light and disposing a second linearly polarising filter in front of the emitter to polarise the unpolarised light.

14. The method of claim 11, wherein the target region of tissue is illuminated with visible light.

15. The method of claim 14, wherein the first spectral range corresponds to a spectral range associated with red light and the second spectral range corresponds to a spectral range associated with green light.

16. The method of claim 11, wherein the linearly polarised light is diffused light.

17. A method of imaging blood within a target region of tissue, comprising the steps:
    restricting blood flow to the target region of tissue with an inflatable cuff;
    illuminating the target region of tissue using linearly polarised light having at least a first spectral range and a second spectral range, such that the linearly polarised light is scattered and/or reflected by the target region of tissue, wherein the absorptivity by blood of light having the first spectral range is less than the absorptivity by blood of light having the second spectral range;
    transmitting by a linearly polarising filter disposed between the target region of tissue and an imaging sensor scattered light which has been depolarised by the target region of tissue and blocking by the linearly polarising filter reflected light which remains polarised;
    receiving with the imaging sensor light scattered and/or reflected by the target region of tissue; and capturing at least one image of at least a portion of the target region of tissue using light which has been transmitted by the linearly polarising filter.

18. The method of claim 17, wherein the linearly polarising filter is arranged such that the plane of polarisation of the linearly polarising filter is orthogonal to the plane of polarisation of the linearly polarised light.

19. The method of claim 18, wherein the step of illuminating the target region of tissue using linearly polarised light comprises the step of using a light emitter configured to emit unpolarised light to emit light and disposing a second linearly polarising filter in front of the emitter to polarise the unpolarised light.

20. The method of claim 17, wherein the target region of tissue is illuminated with visible light.

21. The method of claim 20, wherein the first spectral range corresponds to a spectral range associated with red light and the second spectral range corresponds to a spectral range associated with green light.

22. The method of claim 17, wherein the linearly polarised light is diffused light.

* * * * *